United States Patent
Zhang et al.

(10) Patent No.: US 11,801,308 B2
(45) Date of Patent: Oct. 31, 2023

(54) DRUG DELIVERY VEHICLE, DRUG DELIVERY SYSTEM AND METHODS THEREOF

(71) Applicant: DALIAN MINZU UNIVERSITY, Dalian (CN)

(72) Inventors: Shubiao Zhang, Dalian (CN); Huiying Chen, Dalian (CN); Yinan Zhao, Dalian (CN); Defu Zhi, Dalian (CN); Shaohui Cui, Dalian (CN)

(73) Assignee: DALIAN MINZU UNIVERSITY, Dalian (CN)

( * ) Notice: Subject to any disclaimer, the term of this patent is extended or adjusted under 35 U.S.C. 154(b) by 93 days.

(21) Appl. No.: 17/475,715

(22) Filed: Sep. 15, 2021

(65) Prior Publication Data

US 2022/0265849 A1 Aug. 25, 2022

Related U.S. Application Data

(60) Provisional application No. 63/151,197, filed on Feb. 19, 2021.

(51) Int. Cl.
*A61K 47/61* (2017.01)
*B82Y 5/00* (2011.01)
*A61K 47/69* (2017.01)
*A61K 45/06* (2006.01)

(52) U.S. Cl.
CPC .......... *A61K 47/6911* (2017.08); *A61K 45/06* (2013.01); *A61K 47/61* (2017.08); *B82Y 5/00* (2013.01)

(58) Field of Classification Search
None
See application file for complete search history.

(56) References Cited

PUBLICATIONS

Ramasamy et al., Layer-by-layer coated lipid-polymer hybrid nanoparticles designed for use in anticancer drug delivery, 2014, Carbohydrate Polymers, 102, 653-661 (Year: 2014).*
Yang et al., Enzymatically Disulfide-Crosslinked Chitosan/Hyaluronic Acid Layer-by-Layer Self-Assembled Microcapsules for Redox-Responsive Controlled Release of Protein, 2018, ACS Appl. Mater. Interfaces, 10, 39, 33493-33506 (Year: 2018).*
Aburahma et al., Compritol 888 ATO: a multifunctional lipid excipient in drug delivery systems and nanopharmaceuticals, 2014, Expert Opinion on Drug Delivery, 11(12), 1865-1883 (Year: 2014).*
PubChem "Lecithin from Soybean" (https://pubchem.ncbi.nlm.nih.gov/compound/Lecithin-from-Soybean; accessed Feb. 1, 2023) (Year: 2023).*
PubChem "Polyethylene oxide sorbitan mono-oleate" (https://pubchem.ncbi.nlm.nih.gov/compound/Polyethylene-oxide-sorbitan-mono-oleate; accessed Feb. 1, 2023) (Year: 2023).*
Feng et al., The acidic tumor microenvironment: a target for smart cancer nano-theranostics, 2018, National Science Review, 5(2), 269-286 (Year: 2018).*
Zhao et al., The Future of Layer-by-Layer Assembly: A Tribute to ACS Nano Associate Editor Helmuth Möhwald, 2019, ACS Nano, 13, 6151-6169 (Year: 2019).*
Senthebane et al., The Role of Tumor Microenvironment in Chemoresistance: 3D Extracellular Matrices as Accomplices, 2018, Int. J. Mol. Sci. 19, 2861, 1-32 (Year: 2018).*
An et al., Nanostructural Systems Developed with Positive Charge Generation to Drug Delivery, 2014, Advanced Healthcare Materials, 3(8), 1162-1181 (Year: 2014).*
Kim et al., Hydrophobically modified glycol chitosan nanoparticles as carriers for paclitaxel, 2006, Journal of Controlled Release, 111, 228-234 (Year: 2006).*
Romberg et al., Sheddable Coatings for Long-Circulating Nanoparticles, 2007, Pharmaceutical Research, 25(1), 55-71, DOI: 10.1007/s11095-007-9348-7 (Year: 2007).*

* cited by examiner

*Primary Examiner* — Mark V Stevens
*Assistant Examiner* — Katherine Siller
(74) *Attorney, Agent, or Firm* — HAUPTMAN HAM, LLP

(57) ABSTRACT

Disclosed herein is a drug delivery vehicle. The drug delivery vehicle includes a lipid nanoparticle core for enclosing a primary drug and a protective shell surrounding the lipid nanoparticle. Also disclosed herein is a drug delivery system including the drug delivery vehicle carrying the primary drug, a method of preparing the drug delivery system and a method of using the drug delivery system.

16 Claims, 18 Drawing Sheets

Schematic of HCLR nanocarrier fabrication and the in vivo fate in breast tumor targeting gene delivery (LR: DOTAP/survivin-shRNA; LPR: CS/DOTAP/survivin-shRNA lipopolyplex; CLR: HAase/CS/DOTAP/survivin-shRNA; HCLR: HA/HAase/CS/liposome/survivin-shRNA).

Panels A-C: Synthesis pathway of CMO (A), CLR (B) and HCLR (C).

Panel A: Characterization of chitosan derivatives by FTIR (a) and $^1$HNMR (b)
Panel B: Characterization of HA derivatives by FTIR (a) and $^1$HNMR (b).

Panel A: 1HNMR (a) and FTIR (b) characterization of CMO; Panel B: FTIR characterization of HCLR, HLR and LR; Panel C: TEM (upper row) and SEM (bottom row) characterization of the nanocarriers; Panel D: Sizes (a) and zeta potentials (b) of HCLR, HLR and LR by DLS.

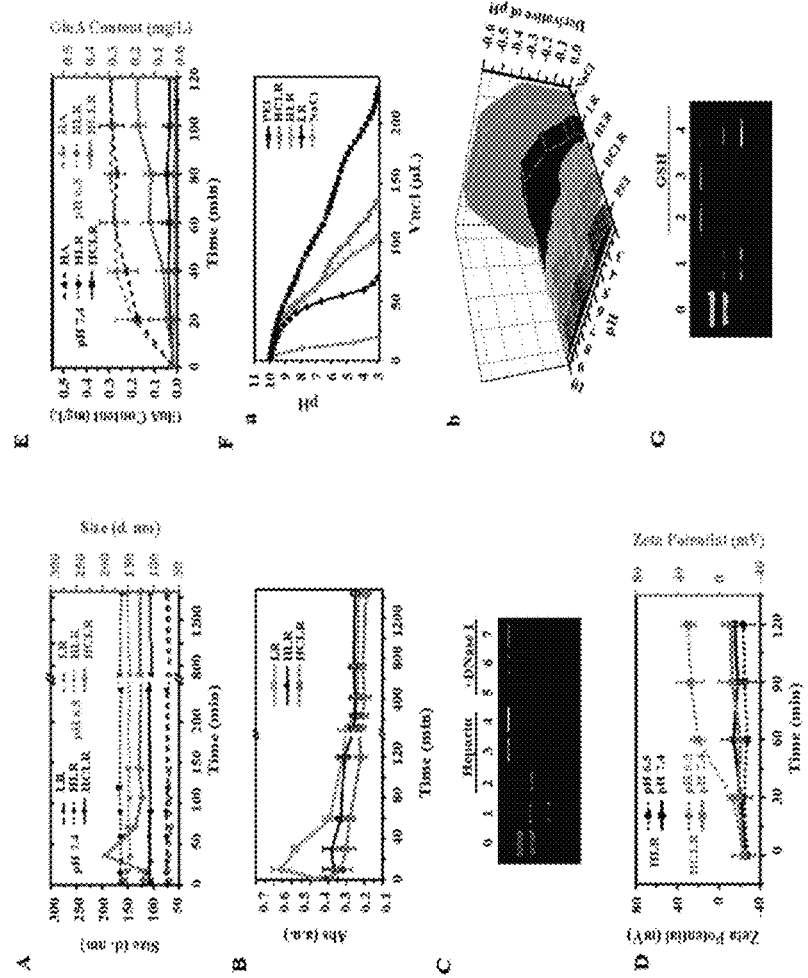

Panel A: Time-dependent size variations of LR, HLR and HCLR in PBS of pH 7.4 and 6.5 by DLS. Panel B: The UV absorbance of the nanocarriers after incubated with the plasma for a set period of time. Panel C: AGE results of the stability evaluation of LR (lane 2&5), HLR (lane 3&6) and HCLR (lane 4&7) in Heparin (10 U/mL), Heparin with Dnase I (0.1 U/μL, 2.0 U); lane 0: marker, lane 1: pDNA. Panel D: ζ potentials of HCLR and HLR nanocarriers after incubated in PBS of pH 7.4 and 6.5 for a set period of time. Panel E: GluA content measured in HCLR and HLR nanocarriers by Morgan-Elson colorimetry method after incubated with HAase for a set period of time. Panel F: Acid-base titration curve (a) and the derivative sketch (b) to determine the proton buffering capacity. Panel G: AGE result of the redox-responsive gene release ability of LR (lane 2), HLR (lane 3) and HCLR (lane 4) measured in GSH (10 mM); lane 0: marker, lane 1: pDNA

Figure 12

Time-dependent size and zeta potential variations of HCLR, HLR and LR in different solutions of DI water (Panel A), 0.154 M NaCl (Panel B), PBS (Panel C), PBS with 10% FBS (Panel D) and DMEM with 10% FBS (Panel E).

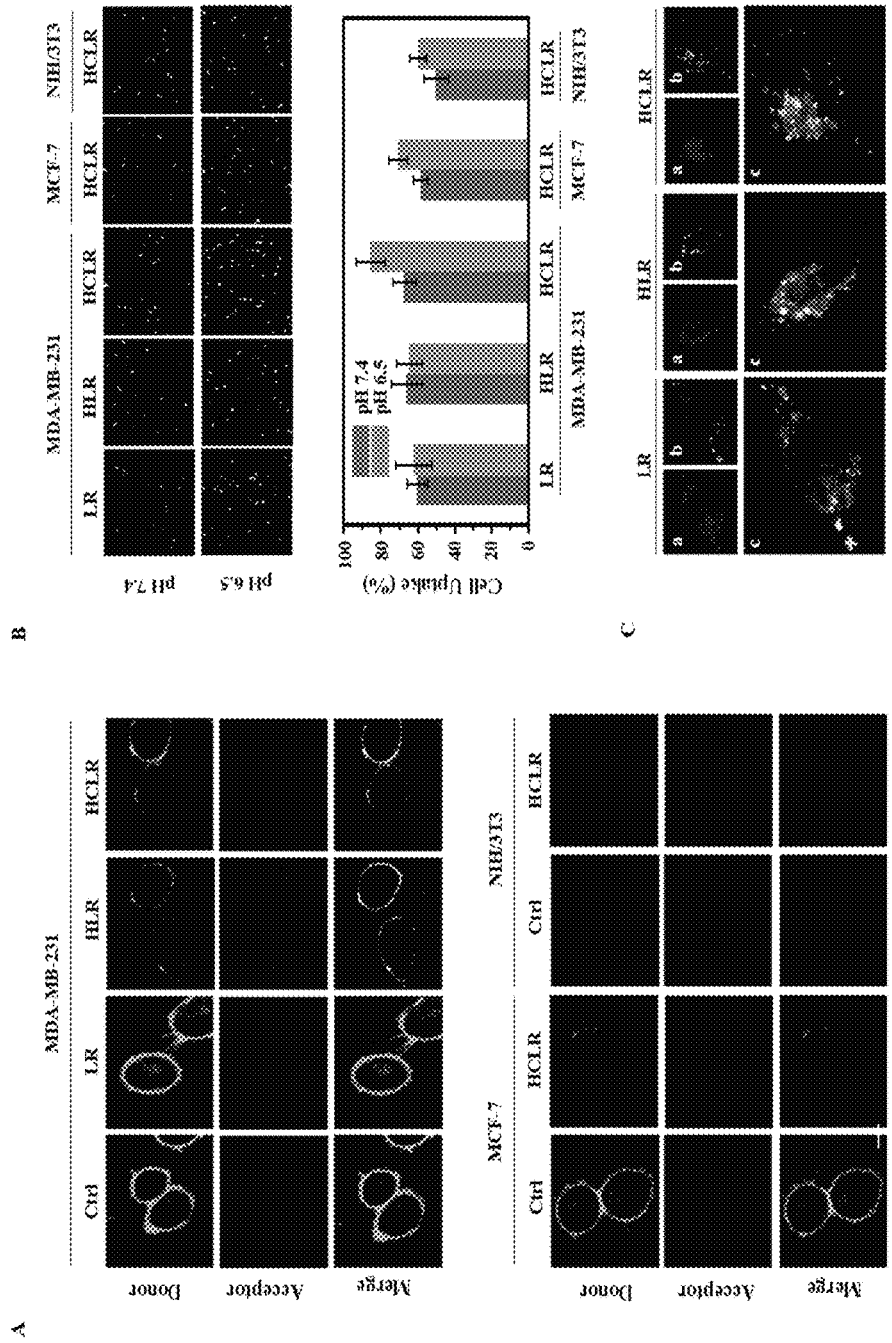

Figure 14

Panel A: Representative CLSM images of the nanocarrier targeting to CD44 receptor of MDA-MB-231 cells (green: CD44 receptor, red: HA shielding nanocarrier), with MCF-7 and NIH/3T3 cells as controls. Panel B: The cell uptake determined by inverted fluorescence microscope (representative images) and flow cytometry of LR, HLR and HCLR nanocarriers in MDA-MB-231 breast cancer cells, with MCF-7 and NIH/3T3 cells as controls. Panel C: Representative images by CLSM to evaluate the lysosome escape of LR, HLR and HCLR nanocarriers in MDA-MB-231 breast cancer cells (a, Lyso-tracker, endo/lysosome; b, FITC, nanocarrier; c, merged).

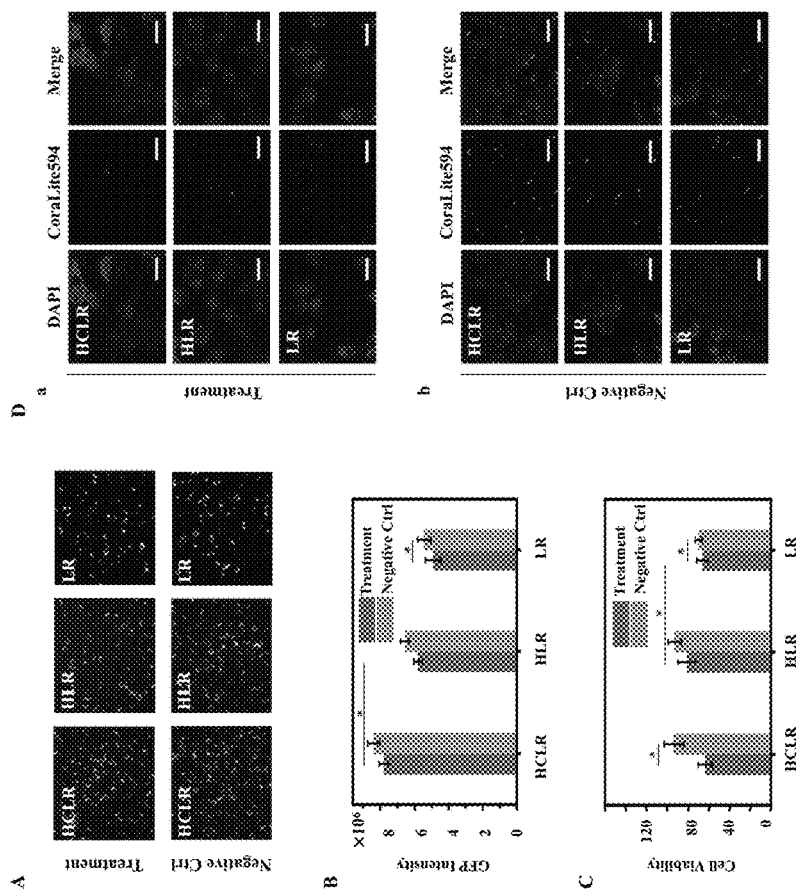

Panel A: Representative inverted fluorescence microscope images of MDA-MB-231 cells transfected by nanocarriers carrying GFP gene after 48 h. Panel B: Quantitative analysis of GFP fluorescence intensity of MDA-MB-231 cells treated by nanocarriers for 48 h. Panel C: CCK-8 cell viability assay of MDA-MB-231 cells transfected by HCLR, HLR and LR, in comparison with negative control group (by replacing shRNA with negative control shNC). Panel D: Representative CLSM images of MDA-MB-231 cells after transfection by HCLR, HLR and LR for 48 h and treated by immunofluorescence staining to detect survivin protein expression (a: treatment group, b: negative control group; blue: nuclei, red: survivin protein; scale bar = 20 μm). *P < 0.05.

Figure 15

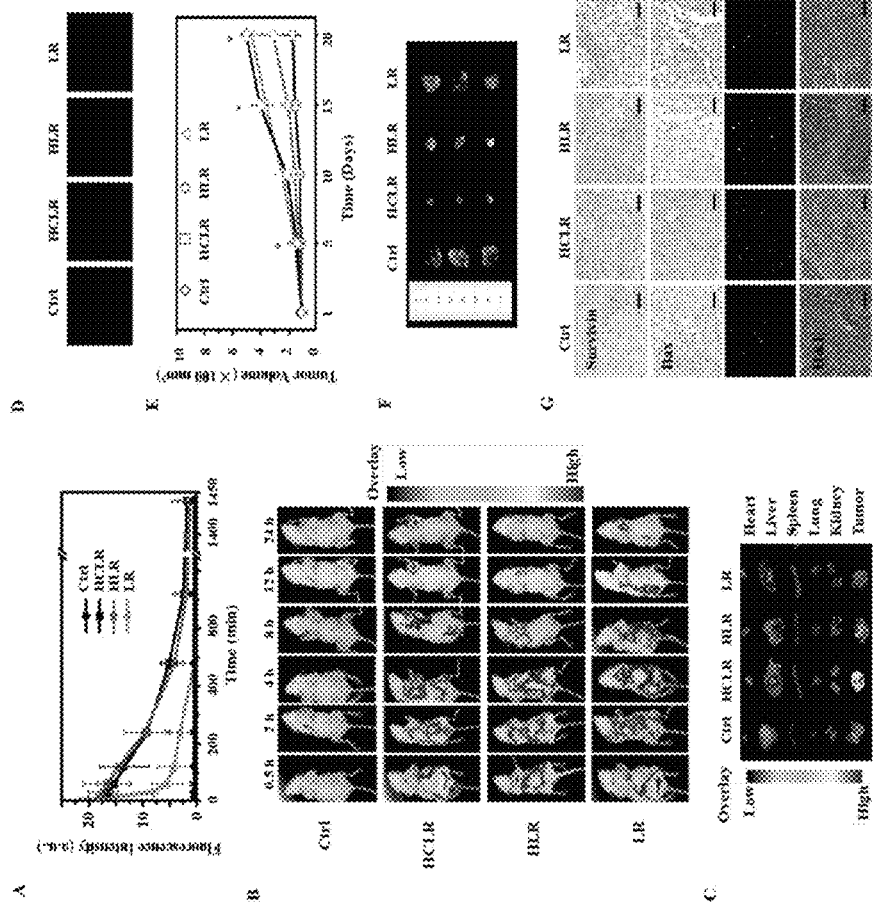

Figure 16

Panel A: The blood clearance curve during 24 h post-injection. Panel B: Fluorescent images of the mice during 24 h after the administration with HCLR, HLR and LR. Panel C: Images of the organs (heart, liver, spleen, lung and kidney) and tumors of the sacrificed mice at 24 h after administration of HCLR, HLR and LR. Panel D: Fluorescent images of whole cross sections of tumors obtained by CLSM. Panel E: Growth curve of MDA-MB-231 xenograft tumor in mice during 20 days after the administration of HCLR, HLR and LR. Panel F: Tumor photos of the mice treated for 20 days. Panel G: IHC, TUNEL and H&E staining analysis for evaluation of *in vivo* anti-proliferation and apoptosis in HCLR, HLR and LR treated groups (scale bar = 100 μm). *$P < 0.05$.

Panel A: Body weight of tumor-bearing mice after 20 days administration of HCLR, HLR and LR. Panel B: Serum analysis of ALT, AST, TB, CREA, BUN and Cys-C. Panel C: Organs H&E analysis, including liver, kidney, lung, spleen and heart (scale bar = 100 μm). $^*P < 0.05$.

DRUG DELIVERY VEHICLE, DRUG DELIVERY SYSTEM AND METHODS THEREOF

PRIORITY CLAIM AND CROSS-REFERENCE

The instant application claims priority from U.S. Provisional Application No. 63/151,197 filed on Feb. 19, 2021, the entirety of which is hereby incorporated herein by reference.

BACKGROUND

Lipid based nanoparticles such as liposomes and micelles have been used as drug delivery systems to deliver drugs into cells. These drug delivery systems, however, face difficulties such as unsatisfactory stability, low specificity and insufficient drug release into cells. When used to treat cancer, these drug delivery systems further face issues with tumor accumulation, tumor penetration, and cell internalization, which lead to the low delivery efficacy.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 12 is graphs of evaluation results of stability and environment-responsive properties of an exemplary drug delivery vehicle in accordance with some embodiments.

FIG. 14 is images and graphs of evaluation results of the cellular uptake of an exemplary drug delivery vehicle in accordance with some embodiments.

FIG. 15 shows the evaluation results of the primary drug delivery efficiency of an exemplary drug delivery vehicle in accordance with some embodiments.

FIGS. 16 and 17 are images and graphs of in vivo tumor targeting and anti-proliferation efficacy evaluation results of a drug delivery system according to some embodiments.

DETAILED DESCRIPTION

Figure 1:
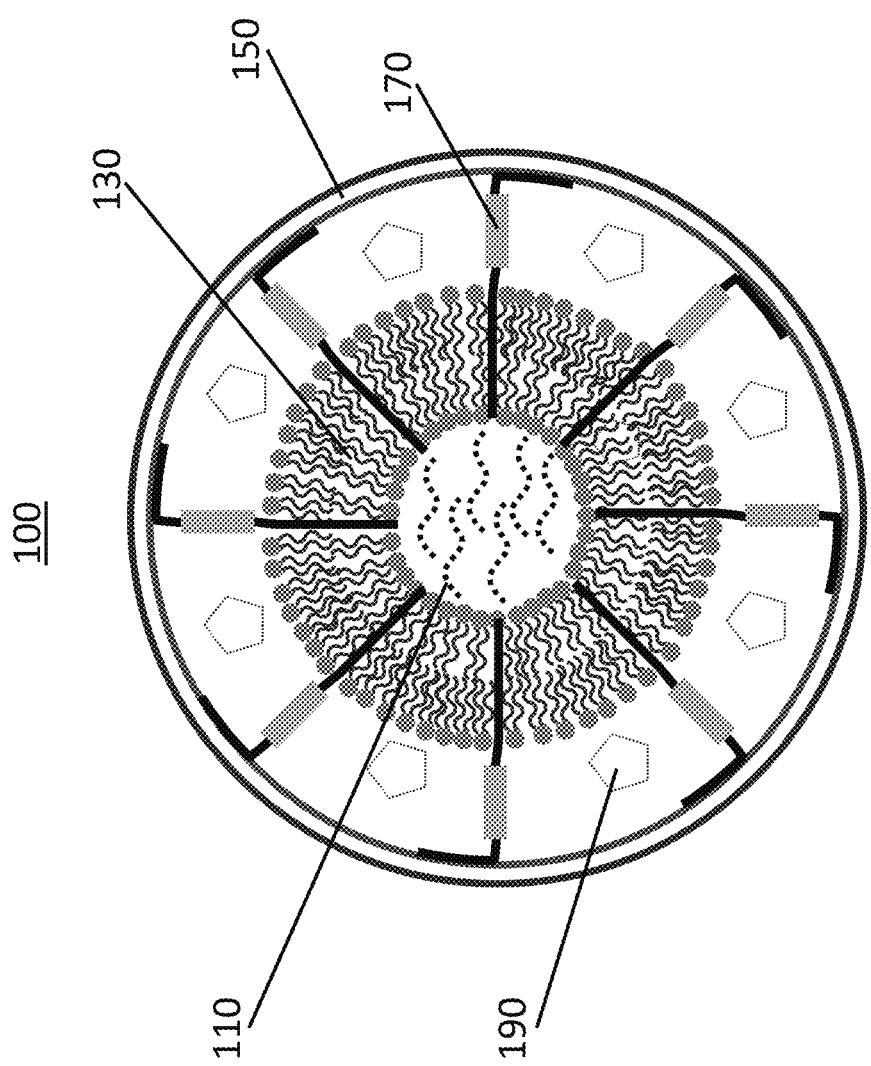
FIG. 1 is a drug delivery vehicle in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Drug Delivery Vehicle

In some embodiments, the instant specification is directed to a drug delivery vehicle.

In some embodiments, the instant specification is directed to a drug delivery vehicle for treating cancer.

Referring to FIG. 1, in some embodiments, the drug delivery vehicle 100 includes a lipid nanoparticle core 130. In some embodiments, the lipid nanoparticle core 130 is configured to enclose a primary drug 110. One of ordinary skill in the art would recognize that the primary drug 110 is not considered as part of the drug delivery vehicle 100.

In some embodiments, the lipid nanoparticle core 130 includes a liposome core, a micelle core, a solid lipid particle core, or combinations thereof.

Figure 2:
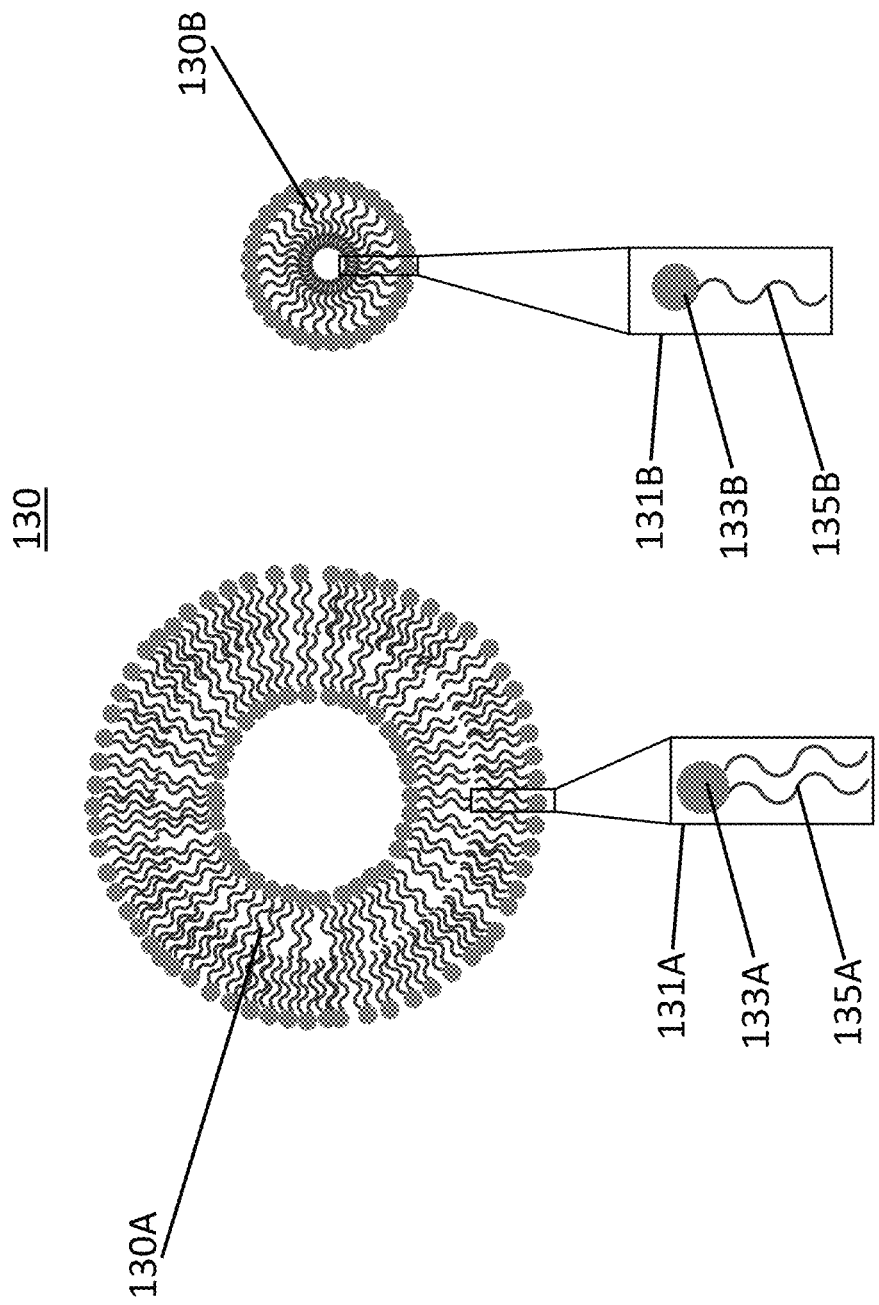
FIG. 2 is a liposome core and a micelle core in accordance with some embodiments.

Referring to FIG. 2, in some embodiments, the lipid nanoparticle core 130 includes a liposome core 130A or a micelle core 130B.

In some embodiments, the nanoparticle core 130 includes the liposome core 130A. A liposome, as used herein, refers to a vesicle having a lipid bilayer, such as a single lipid bilayer. In some embodiments, the liposome 130A is configured to enter a cell, such as a mammalian cell, via endocytosis, thereby delivering the primary drug 110 into the cell. In some embodiments, the liposome 130A is configured to deliver the primary drug 110 into the cell by releasing the primary drug 110 in the cytosol through by fusing with the cell membrane. Since the primary drug 110 is not part of the drug delivery vehicle 100, the primary drug 110 will be described in the "Drug Delivery System" section below.

In some embodiments, the lipid component 131A that forms the liposome 130A includes a hydrophilic head 133A and a hydrophobic tail 135A. As such, the liposome core 130A, when suspended in an aqueous environment, has an outer hydrophilic portion facing the aqueous environment and an inner hydrophilic portion facing inwardly. The hydrophobic tails of lipid component 131A form a hydrophobic portion which is sandwiched by the two hydrophilic portions. The liposome 130A is able to enclose primary drugs 110 that dispersed in an aqueous solution, such as primary drugs 110 dissolved in the aqueous solution.

In some embodiments, the lipid component 131A that forms the liposome includes one hydrophilic head 133A and two hydrophobic tails 135A. However, the instant specification is not limited thereto. One of ordinary skill in the art would understand that, in some embodiments, the lipid component 131A can include one or more than two hydrophobic tails 135A.

In some embodiments, the lipid component 131A includes a cationic lipid, an anionic lipid, or combinations thereof.

A cationic lipid is one that includes a positively charged head group. In some embodiments, the liposome core 130A including cationic lipid is used for enclosing a primary drug 110 that is negatively charged, although there is no absolute requirement for this match. Negatively charged primary drugs 110 include nucleotides (such as DNA, RNA or negatively charged analogous of DNA/RNA molecules), negatively charged peptides, small molecules having a molecular weight of 900 doltons or less that are negatively charged, proteins having negative surface charges, and so on.

Examples of cationic group on the head of lipid component 131A includes quaternary ammoniums, amines, amino acids, peptides, guanidinium, positively charged heterocyclic headgroups, positively charged saccharide groups, or other types of positively charged groups. In some embodiments, the cationic group is part of the lipid head. In some embodiments, the cationic group is attached to the head of the lipid via modification to the lipid molecule.

Examples of cationic lipids include 1,2-di-O-octadecenyl-3-trimethylammonium propane (DOTMA), 1,2-Dioleoyl-sn-glycero-3-phosphoethanolamine (DOPE), dioleoyl-3-trimethylammonium propane (DOTAP), 1,2-dimyristyloxy-propyl-3-dimethyl-hydroxy ethyl ammonium bromide (DMRIE), DOGS, 2,3-dioleyloxy-N-[2(sperminecarboxamido)ethyl]-N,N-dimethyl-1-propanaminium triflouroacetate (DOSPA), dimethyldioctadecylammonium bromide (DDAB), 0,0'-ditetradecanoyl-N-(α-trimethylammonioacetyl)diethanolamine chloride (DC-6-14), 1,2-dioleoyl-sn-glycero-3-phosphocholine (DOPC), 1-stearoyl-2-oleoyl-sn-glycero-3-phosphocholine (SOPC), 1,2-Distearoyl-sn-glycero-3-phosphocholine (DSPC), 3β[N—(N',N'-dimethylaminoethane)-carbamoyl]cholesterol (DC-Chol), 1,2-Dioleoyloxy-3-dimethylaminopropane (DODAP), or 1,2-Dioleyloxy-3-dimethylaminopropane (DODMA).

An anionic lipid is one that includes a negatively charged head group. In some embodiments, liposome core 130A including anionic lipid is used to enclose primary drug 110 that is positively charged, although matching the charge between the lipid and the primary drug is not required. Positively charged primary drugs 110 include positively charged peptides, small molecules having a molecular weight of 900 doltons or less that are positively charged, proteins having positive surface charges, and so on.

Examples of anionic groups for the head for lipid component 131A includes phosphate group, sulfate group, sulfonate group, negatively charged saccharide groups, carboxyl group, or other types of negatively charged groups.

Examples of anionic lipids include phospholipids such as phosphatidic acid (PA), phosphatidylethanolamine (PE), phosphatidylcholines (PC) (such as 1,2-dimyristoyl-sn-glycero-3-phosphocholine (DMPC), dipalmitoylphosphatidylcholine (DPPC) or distearoylphosphatidylcholine (DSPC)), phosphatidylserine (PS), phosphoinositides (e.g., phosphatidylinositol (PI), phosphatidylinositol monophosphates (PIP), phosphatidylinositol bisphosphates (PIP$_2$) and phosphatidylinositol trisphosphate (PIP3)), sphingolipids, phosphatidylglycerols or phosphatidylserines; acidic cholesteryl esters such as cholesteryl hemisuccinate; lipid sulfates such as chlorosulfolipids; and sulfonolipids such as taurolipids.

Referring to FIG. 2, in some embodiments, the lipid nanoparticle core 130 includes a micelle core 130B. A micelle, as used herein, is an aggregate of an amphiphilic surfactant 131B having a hydrophilic head 133B and a hydrophobic tail 135B. In some embodiments, the micelle core 130B is substantially spherical. In an aqueous environment, the hydrophilic head 133B forms a hydrophilic portion facing the aqueous environment, and the hydrophobic tail 135B forms a hydrophobic portion enclosed by the hydrophilic portion. The hydrophobic portion of the micelle 130B is able to carry a hydrophobic primary drug 110, such as a hydrophobic peptide, a small molecule having a molecular weight of 900 doltons or less that is hydrophobic, a protein having a hydrophobic surface, and so on.

In some embodiments, the surfactant 131B includes one hydrophilic head 133B and one hydrophobic tail 135B. However, the instant specification is not limited thereto and, in some embodiments, the surfactant 131B includes more than one hydrophobic tail 135B. In some embodiments, the surfactant 131B is a polymerizable monomer and the micelle 130B is formed by polymerizing the surfactant 131B, such as polymerizing the surfactant 131B in an aqueous environment. In some embodiments, the micelle 130B is formed by a monomer surfactant 131B without polymerization.

Referring to FIG. 1, in some embodiments, the drug delivery vehicle further includes a protective shell 150 surrounding the lipid nanoparticle core 130. Currently, liposomes and micelles are utilized in a substantial percentage of the ongoing clinical trials in gene therapy for treating cancers. However, leakage of the enclosed material in circulation and the sub-decomposition of the complex inside cells are a common problem for these types of drug delivery. The protective shell 150 surrounding the lipid nanoparticle core 130 increases the stability of the liposome 130 in the circulation and thereby reducing the leakage and decomposition of the primary drug 110 in the circulation, which in turn improves delivery of the primary drug 110 to the desired site and reduces the potentially harmful exposure of healthy cells to the primary drug 110.

In some embodiments, the protective shell 150 entirely surrounds the lipid nanoparticle core 130, while in other embodiments, protective shell 150 partially surrounds the lipid nanoparticle core 130.

In some embodiments, the protective shell 150 includes a polymer. In some embodiments, the polymer of the protective shell 150 includes a polysaccharide or a poly(amino acid).

In some embodiments, the protective shell 150 is breakable by an extracellular environment specific to a cancer cell or a cancer tissue. Examples of such extracellular environments include the presence of cancer specific extracellular enzymes or an acidic pH.

In some embodiments, the protective shell 150 includes a peptide bond cleavable by an extracellular protease secreted by a cancer cell or otherwise specific to an extracellular environment of a cancer tissue. In some embodiments, the structure integrity of the protective shell 150 uses the peptide bond. Some types of cancer show increased activity of specific extracellular proteases and decreased activity of the opposing endogenous inhibitors. According to these embodiments, when the drug delivery vehicle is in close proximity to the cancer cells, the increased presence of the extracellular protease (in conjunction with the decrease inhibition of enzymatic activities thereof) cleaves the peptide bond and thereby fully or partially exposing the lipid nanoparticle core 130. Examples of the cancer specific extracellular proteases include certain members of matrix metalloproteinases (such as MMP-7). One of ordinary skill in the art would understand how to design peptides that are cleavable by these proteases as the target sequences of such proteases are known in the art.

In some embodiments, the structure of the protective shell 150 includes a polymer that is breakable by an acidic pH, such as a pH ranging from 6 to 6.9, such as a pH ranging from 6.5 to 6.8. A reduction in extracellular pH (pHe) is a characteristic of many solid tumor cancers. The pHe of the cancer microenvironment is typically in the range of 6.5 to 6.8, in contrast to the pHe range of 7.2 to 7.5 for most normal tissues. The acidic pHe is a result of increased lactic acid production by high aerobic glycolysis and poor perfusion, which are common among solid cancers. One example of a polymer that is breakable by this slightly acidic pHe is hyaluronic acid (HA). Therefore, in some embodiments, the protective shell 150 includes hyaluronic acid.

In some embodiments, the structure of the protective shell 150 includes a polysaccharide that is cleavable by an extracellular enzyme specific to a cancer. For example, the level of hyaluronidase, the extracellular enzyme that catalyze the degradation of hyaluronic acid (HA), is increased in cancers such as colorectal, bladder, prostate, breast and brain cancers. Therefore, in some embodiments, the protective shell 150 includes hyaluronic acid.

In some embodiments, protective shell 150 includes a cancer cell targeting motif. As used herein, a cancer cell targeting motif is a motif that specifically interacts with the cancer cells or the surrounding environments specific to cancer tissues. The cancer cell targeting motif interacts with the cancer cells or surroundings thereof, causing the drug delivery vehicle 100 to be enriched at the site of the cancel cells. Examples of suitable cancer cell targeting motifs includes a peptide, an aptamer, an oligo-saccharide or a polysaccharide that interacts with a surface marker of a cancer cell, such as a surface protein specific to the cancer cell or a surface protein overexpress in the cancer cell in comparison to normal cells.

Figure 3:
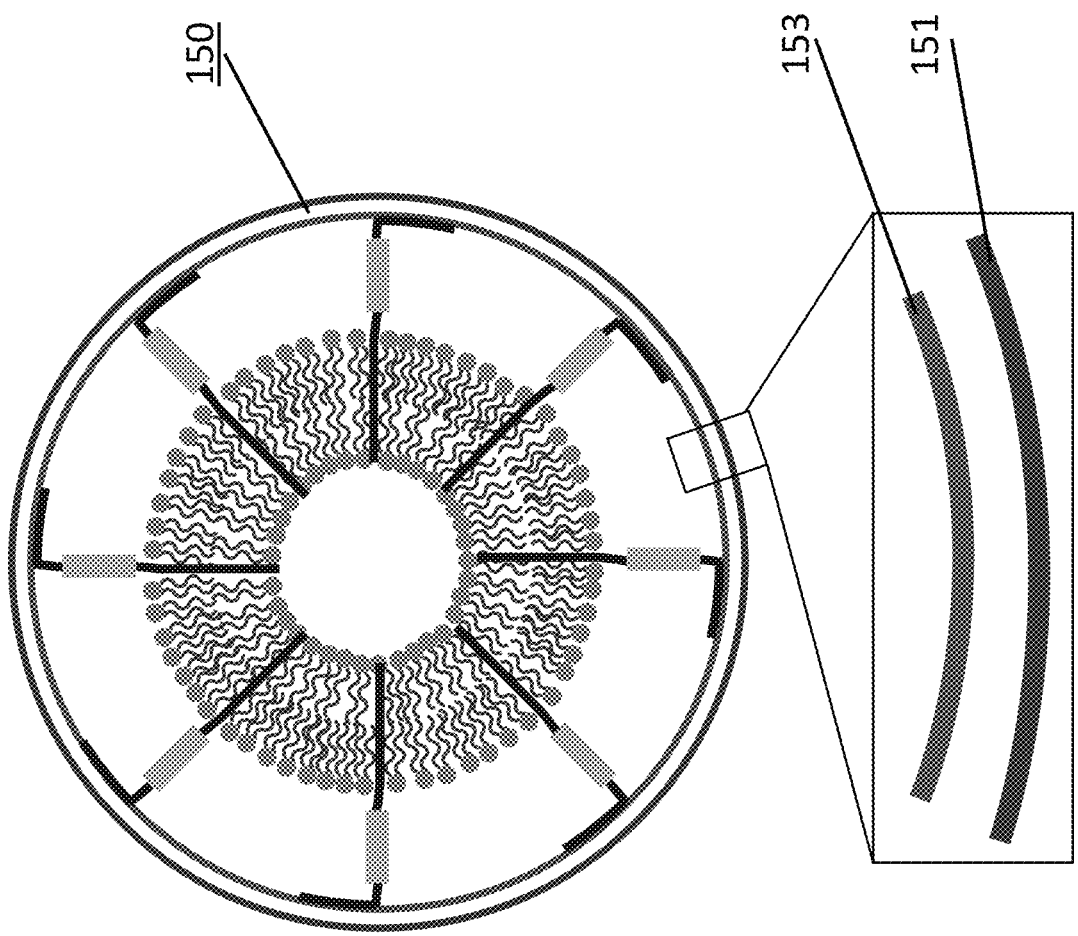
FIG. 3 is protective shell in accordance with some embodiments.
Figure 4:
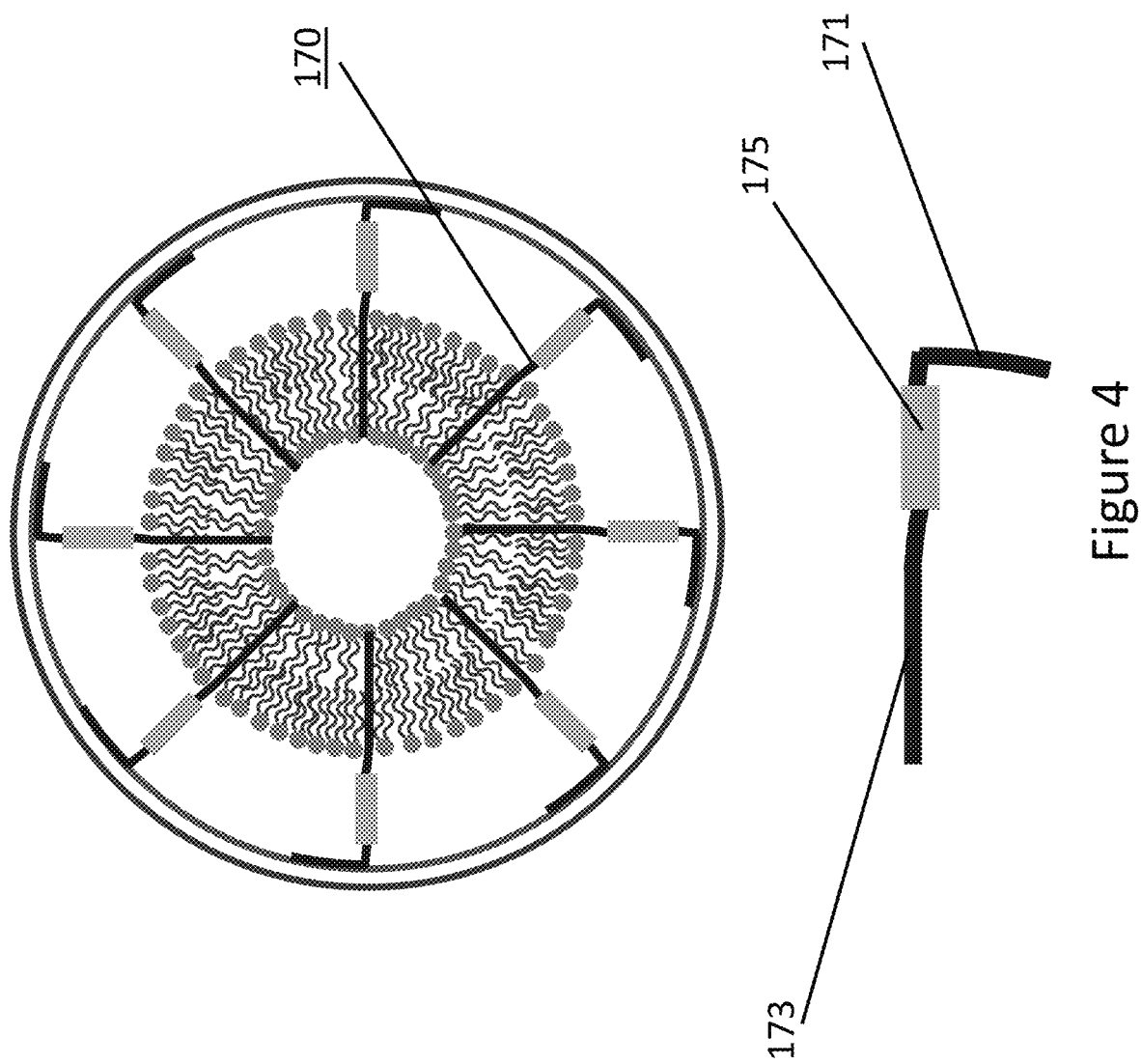
FIG. 4 is a linkage for connecting a protective shell to a liposome core or a micelle core in accordance with some embodiments.

Referring to FIG. 3, in some embodiments, the protective shell 150 includes an outer layer 151 and an inner layer 153.

In some embodiments, the outer layer 151 has a neutral charge or a negative charge. Negative or neutral charged surface often increases the stability of the drug delivery vehicle in the blood circulation, and thus reduces the loss of the primary drug 110 before reaching the desired site of delivery. In some embodiments, the inner layer 151 includes hyaluronic acid, which has a negative charge at normal physiologic pH of 7.2 to 7.5.

In some embodiments, the inner layer 153 has a positive charge. Positive surface charge on nanoparticles is known to promote the cell uptake of the nanoparticles and decrease the efflux thereof. In some embodiments, the inner layer 153 includes polylysine, such as poly-L-lysine (PLL), or chitosan.

In some embodiments, the inner layer 153 includes chitosan. Chitosan is a natural polymer of glucosamine and N-acetyl glucodamine. Chitosan has good biocompatibility, mucoadhesiveness and pH-sensitive amino group protonation at pathological microenvironments. The instant inventors have found that chitosan-coated-liposome nanoparticles, when comparing with liposome alone, showed enhanced gene release in the nuclei, as well as improved gene transfection efficiency.

Referring to FIG. 1, in some embodiments, the drug delivery vehicle 100 is configured such that a space between the lipid nanoparticle core 130 and the protective shell 150 is able to enclose a secondary drug 190.

As detailed above, in some embodiments, the protective shell 150 of the drug delivery vehicle 100 is breakable by an extracellular environment specific to a cancer cell or a cancer tissue. According to these embodiments, when the drug delivery vehicle 100 is in proximity with a cancer cell or penetrated into a cancer tissue, the extracellular environment breaks the protective shell 100 of the drug delivery system 100. As such, when a secondary drug 190 is enclosed in the space between the lipid nanoparticle core 130 and the protective shell 150, the extracellular environment of the cancer cell or cancer tissue breaks the protective shell 150, causing the secondary drug 190 to be released. Since the secondary drug 190 is not part of the drug delivery vehicle 100, the secondary drug 190 will be described in the "Drug Delivery System" section below.

In some embodiments, the drug delivery vehicle 100 further includes a linkage 170 connecting the protective shell to the liposome core.

In some embodiments, the linkage 170 includes a shell portion 171 configured to anchor in the protective shell 150, a hydrophobic portion 173 configured to anchor in the lipid nanoparticle 130, as well as intermediate portion 175 linking the shell portion 171 and the hydrophobic portion 173. In some embodiments, the shell portion 171, the intermediate portion 175 and the hydrophobic portion 173 are sequentially connected in this order by covalent bonds.

In some embodiments, the shell portion 171 of the linkage 170 is derived from a material used for forming the shell portion 150, such as derived from a polysaccharide or a poly(amino acid). In some embodiments, the shell portion 171 is derived from hyaluronic acid or chitosan.

In some embodiments, the shell portion 171 is derived from chitosan. As detailed above, in some embodiments, when the drug delivery vehicle 100 is in close proximity to a cancer cell or a cancer tissue, the extracellular environment of the cancer cell or cancer tissue breaks the protective shell 150. According to these embodiments, the linkage 170 is still attached to the lipid nanoparticle core 130 after the breakage of the protective shell 150, and the shell portion 171 derived from chitosan can provide the lipid nanoparticle core 130 with a surface positive charge, thereby promoting the uptake and enhance the delivery.

In some embodiments, the inner layer 153 of the protective shell 150 is entirely formed by the shell portion 171 of the linkage 170. In some embodiments, the inner layer 153 of the protective shell 150 is formed by the shell portion 171 of the linkage 170 in conjunction with another component.

In some embodiments, the linkage 170 is cleavable by an intracellular stimulus. After entering the cell via endocytosis, the linkage 170 embedded lipid nanoparticle 130 sometimes releases the enclosed primary drug 110 less efficiently than the lipid nanoparticle 130 alone. As such, making the linkage 170 cleavable by an intracellular stimulus removes this obstacle to drug release posed by the linkage 170.

In some embodiments, the intermediate portion 175 linking the shell portion 171 and the hydrophobic portion 173 is cleavable by the intracellular stimulus.

In some embodiments, the linkage 170 is cleavable by an intracellular protease, or by an intracellular redox potential.

In some embodiments, the intermediate portion 175 is cleavable by an intracellular protease, or by an intracellular redox potential.

In some embodiments, the linkage 170 includes a disulfide bond. In some embodiments, the intermediate portion 175 includes a disulfide bond. Due to the chemically reducing environment inside the cells, exposed disulfide bond —S—S— is reduced to two —SH groups and thereby cleaved.

In some embodiments, the hydrophobic portion 173 includes a C6 to C30 alkyl group, a C6 to C30 alkenyl group, a C6 to C30 alkynyl group, a C6 to C30 aryl group, and derivatives thereof. In some embodiments, hydrophobic portion 173 includes a derivative of a fatty acid, such as an ester of a fatty acid or a derivative thereof. The choice of the hydrophobic portion 173 is based on the compatibility of the hydrophobic portion 173 and the lipid nanoparticle 130. One of ordinary skill in the art knows how to select the hydrophobic portion 173 based on the components used to construct the lipid nanoparticle 130.

In some embodiments, an average size of the drug delivery vehicle 100 ranges from 50 nm to 300 nm. If the average size of the drug delivery vehicle 100 is lower than 50 nm, renal clearance of the drug delivery vehicle 100 by kidney glomeruli removes the delivery vehicle 100 from the system becomes excessive, which can undesirably lower the circulation time of the drug delivery vehicle 100 in the blood. If the average size of the drug delivery vehicle 100 is larger than 300 nm, the large size of the drug delivery vehicle 100 can result in undesirably low tissue penetration efficiency, which is detrimental to treating solid cancer because the drug delivery vehicle 100 needs to penetrate into the tumor tissue to deliver sufficient amount of the carried drug to all cancer cells. In some embodiments, the average size of the drug delivery vehicle 100 ranges from 80 nm to 250 nm. In some embodiments, the average size of the drug delivery vehicle 100 ranges from 100 nm to 200 nm. When the average size of the drug delivery vehicle 100 is from 100 nm to 200 nm, a desirable balance between sufficient circulation time and sufficient tissue penetration efficiency can be achieved.

Drug Delivery System

In some embodiments, the instant specification is directed to a drug delivery system.

In some embodiments, the instant specification is directed to a drug delivery system for treating cancer.

Figure 5:
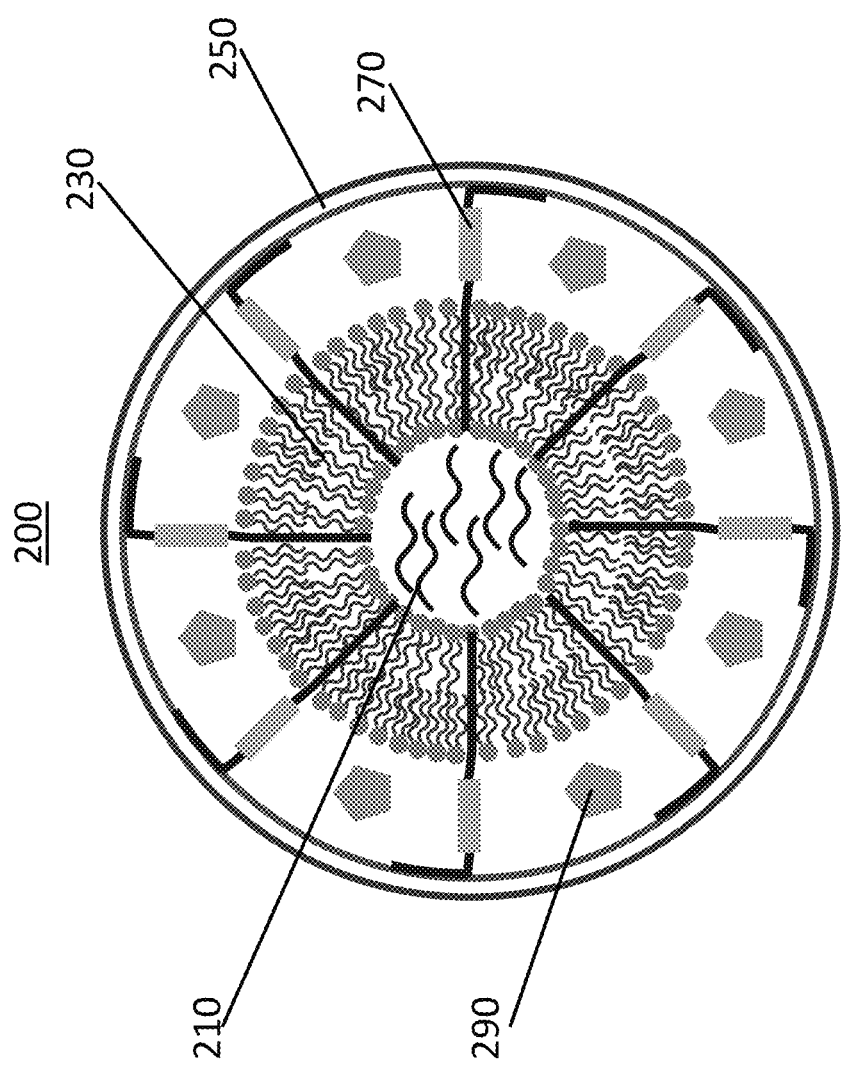
FIG. 5 is a drug delivery system in accordance with some embodiments.

Referring to FIG. 5, in some embodiments, the drug delivery system 200 includes a drug delivery vehicle and a primary drug 210. In some embodiments, the drug delivery vehicle is the same or similar to those as described above in the "Drug Delivery Vehicle" section.

For example, in some embodiments, the drug delivery system 200 includes a lipid nanoparticle core 230 the same as or similar to the lipid nanoparticle core 130 as described above, as well as the primary drug 210.

In some embodiments, the drug delivery system 200 further includes a protective shell 250 the same as or similar to the protective shell 150 as described above.

In some embodiments, the drug delivery system 200 further includes a linkage 270 connecting the protective shell 250 to the lipid nanoparticle core 230. According to these embodiments, the linkage 270 is the same as or similar to those as described above.

In some embodiments, the primary drug 210 is a drug that functions inside a cell. As described above, the lipid nanoparticle 230 is configured such that the lipid nanoparticle 230 fuses with the cell membrane and release the primary drug 210 into the cytosol, or such that the lipid nanoparticle 230 is endocytosed by the cell to allow the primary drug 210 to enter into the cell.

Since according to some embodiments, the drug delivery system 200 is a drug delivery system for treating cancer, in some embodiments, the primary drug 210 is a drug that cases cell death when entering the cancer cell.

In some embodiments, the primary drug includes a chemotherapy agent, a nucleotide sequence that specifically inhibits an oncogene or a proto-oncogene, and so on.

Examples of chemotherapy agents include Actinomycin-D, Alkeran, Ara-C, Anastrozole, Asparaginase, chemotherapy BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, Xeloda, and so on.

In some embodiments, the nucleotide sequence that specifically inhibits an oncogene or a proto-oncogene include an RNA molecule that causes RNA interference. RNA interference refers to the biological process in which RNA molecules cause sequence-specific suppression of gene expression via translation or transcriptional repression. Examples of RNA that causes RNA interference includes a micro-RNA (miRNA), a small interfering RNA (siRNA), a short hairpin RNA (shRNA), and so on. Since the methods for designing miRNA, siRNA and shRNA are well known, and the tools are widely available, one of ordinary skill in the art is able to design the miRNA, the siRNA or the shRNA, as long as the target oncogene or proto-oncogene is chosen, and the sequences of the genes are available.

In some embodiments, the nucleotide sequence that specifically inhibits an oncogene or a proto-oncogene further includes an expression system that specifically disrupts the genomic DNA of the oncogene or the proto-oncogene based on clustered regularly interspaced short palindromic repeats (CRISPR). Such expression systems are configured to express a Cas 9 protein or a Cas 12 protein, as well as a guide RNA (gRNA) that target the Cas protein to the genomic sites of the oncogene or the proto-oncogene that is complementary with the spacer portion of the gRNA. Although using CRISPR to disrupt genomic sites of oncogene or the proto-oncogene requires that the genomic sites to have certain features, such as the presence of a protospacer adjacent motif (PAM) sequence, one of ordinary skill in the art are able to choose oncogenes or proto-oncogenes based on the existence of suitable PAM sequences. Since the methods for designing CRISPR systems are well known and the tools for doing so are widely available, one of ordinary skill in the art is able to design the CRISPR system, as long as the target oncogene or proto-oncogene is chosen, and the sequences of the genes are available.

As used herein, the term "oncogene" means a gene that, in certain circumstances, can transform a cell into a cancer cell, a gene that inhibits the apoptosis of a cancer cell, or a gene that allow a cancer cell to evade the host immune system. As used herein, the term "proto-oncogene" means a normal gene that could become an oncogene due to mutations or increased expression. Examples of oncogenes and proto-oncogenes include the Ras family (e.g., K-Ras, H-Ras, N-Ras), Her2, Myc, Cyclin D, Cyclin E, BCR/ABL, EGFR, B-Raf, MITF, PDL1, Survivin, Bak, Bax, BCMA, Nectin-4, PDGF-R α, and so on.

In some embodiments, the drug delivery system 200 further includes, between the lipid nanoparticle core 230 and the protective shell 250, a secondary drug 290.

In some embodiments, the secondary drug 290 is a drug that functions in an extracellular environment.

In some embodiments, the secondary drug 290 is a drug that functions in an extracellular environment of a cancer cell or a cancer tissue. As detailed above, in some embodiments, the protective shell 250 of the drug delivery system 200, like the protective shell 150 of the drug delivery vehicle 200, is breakable by an extracellular environment specific to a cancer cell or a cancer tissue. According to these embodiments, when the drug delivery system 200 is in proximity with a cancer cell or penetrated into a cancer tissue, the extracellular environment breaks the protective shell 250 of the drug delivery system 200 and release the secondary drug 290.

In some embodiments, the secondary drug 290 includes an antibody, such as a monoclonal antibody, a polyclonal antibody or a humanized antibody, an antigen-binding fragment (e.g., Fab, F(ab')$_2$ or Fab') of an antibody, an antigen binding site (e.g., scFv, di-scFv, sdAb), and so on. In some embodiments, the antibody, the antigen-binding fragment or the antigen binding site is an anticancer antibody, antigen-binding fragment or antigen binding fragment. In some embodiments, the antibody, the antigen-binding fragment or the antigen binding site are those that have specificity for EGFR, PD-1, PD-L1, BCMA, VEGF, CD3, Nectin-4, and so on. By localized releasing of the anticancer antibody/antigen-binding fragment/antigen binding site in proximity to the cancer cells or the cancer tissues, the drug delivery system 200 is able to increase the concentration of the anticancer antibody/antigen-binding fragment/antigen binding site at the site of disease while maintaining a relatively low concentration of the secondary drug 290 near the healthy cells, thereby increase the efficacy of the secondary drug 290 while lowering the extent of the side effects.

In some embodiments, the secondary drug 290 includes an enzyme capable of breaking down an extracellular matrix (ECM). In some embodiments, the secondary drug includes an enzyme capable of breaking down the ECM of a cancer tissue. Increased ECM deposition is a characteristic observed in many types of solid tumors. The increased ECM deposition poses difficulties for nanoparticle-based drug delivery systems, as the nanoparticles, especially nanoparticles of larger diameters, have difficulty passing the ECM and penetrating deep into the solid tumor. By releasing the secondary drug 290 outside the cancer cells to break down the cancer ECM, the drug delivery system 200 is able to penetrate deep into the cancer tissues.

In some embodiments, the secondary drug includes hyaluronidase (HAase). Increased levels of one ECM component, namely hyaluronan (HA), leads to reduced elasticity of tumor tissue and increased interstitial fluid pressure. The instant inventors have discovered that releasing HAase at cancer site significantly alleviates the intratumoral penetration problems commonly encountered by nanoparticle-based drug delivery systems.

Method of Preparing Drug Delivery System

In some embodiments, the instant specification is directed to a method of preparing a drug delivery system.

In some embodiments, the drug delivery system is the same as or similar to the drug delivery system 200 as described above in the "Drug Delivery System" section.

Figure 6:
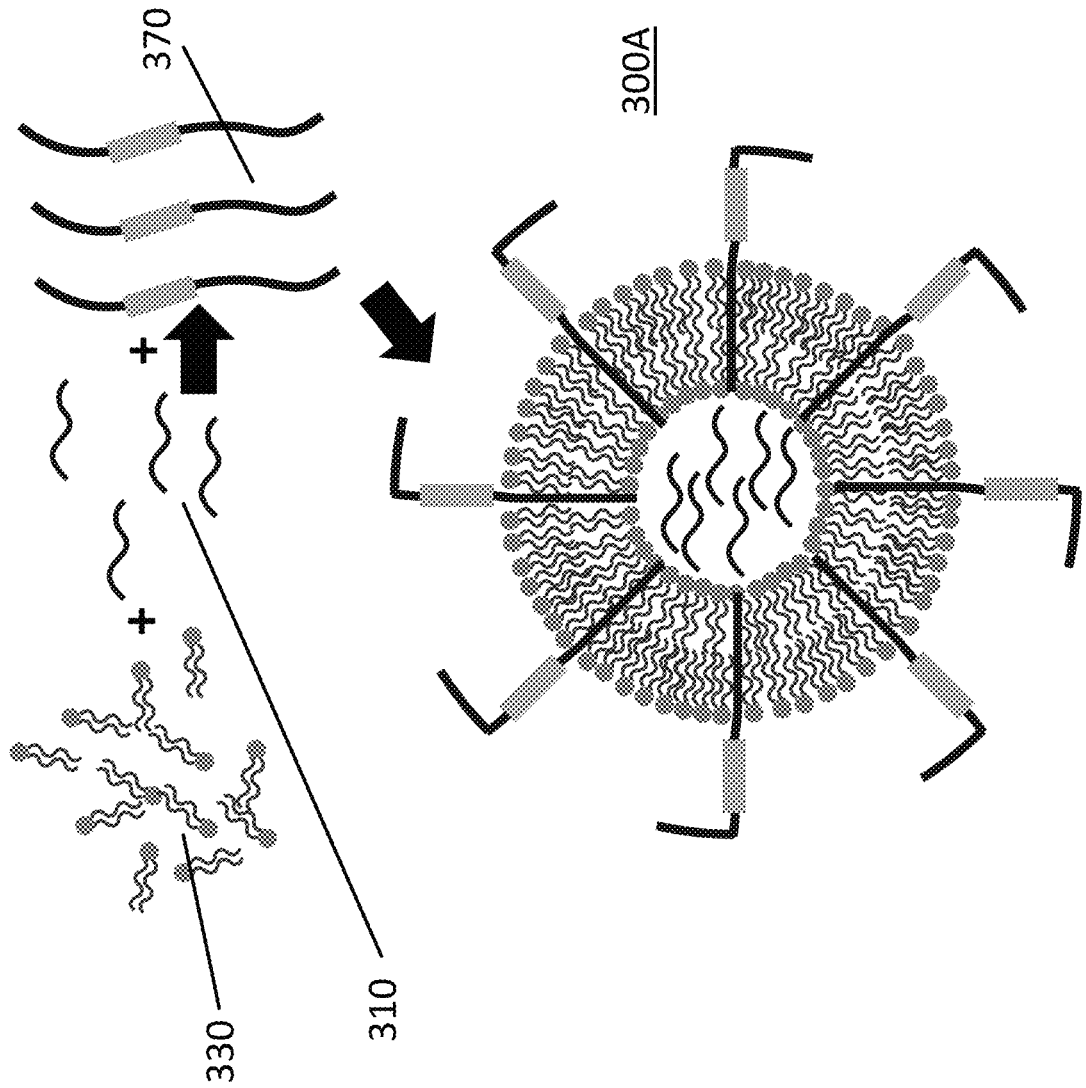
FIGS. 6 and 7 are schematic drawings of a process for making a drug delivery system in accordance with some embodiments.
Figure 7:
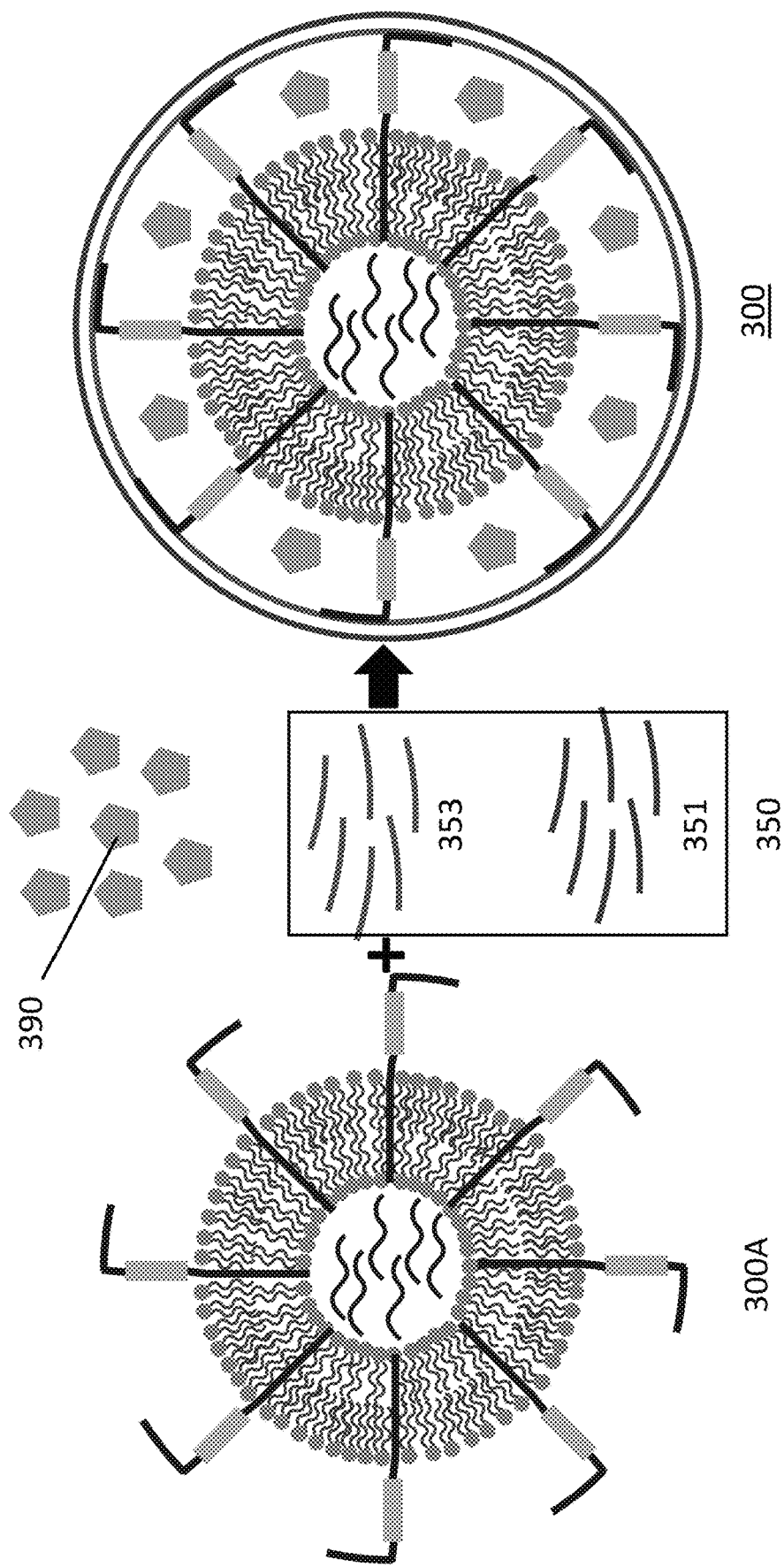

Referring to FIGS. 6 and 7, in some embodiments, the method of preparing a drug delivery system 300 includes forming a primary drug-enclosing lipid nanoparticle core 300A.

Referring to FIG. 7, in some embodiments, forming the primary drug-enclosing lipid nanoparticle core 300A includes preparing a mixture including a component 330 for forming the lipid nanoparticle core and a primary drug 310. In some embodiments, the mixture is prepared in an aqueous environment.

In some embodiments, the mixture further includes a component 370 for forming the linkage such that a primary drug-enclosing lipid nanoparticle core 300A including the lipid nanoparticle, the linkage and the primary drug is formed by one single step. In some embodiments, the drug-enclosing lipid nanoparticle core 300A is formed without the component 370 for forming the linkage, and the component 370 for forming the linkage is incorporated into the primary drug-enclosing lipid nanoparticle core 300A in a separate step after the formation of the drug-enclosing lipid nanoparticle core 300A.

In some embodiments, the formation of the lipid nanoparticle from the component 330 requires polymerization of the component 330. According to some embodiments, the component 330 for forming the lipid nanoparticle core and a primary drug 310 are mixed together before the polymerization reaction starts, and the component 370 for forming the linkage can be included in the mixture before the reaction, or incorporated into the primary drug-enclosing lipid nanoparticle after the polymerization reaction. These embodiments are relevant when the nanoparticle includes, for example, a micelle nanoparticle.

Referring to FIG. 7, in some embodiments, the method of preparing the drug delivery system 300 further includes forming a protective shell around the primary drug-enclosing lipid nanoparticle core 300A.

In some embodiments, forming the protective shell around the primary drug-enclosing lipid nanoparticle core 300A includes preparing a mixture including the primary drug-enclosing lipid nanoparticle core 300A with a component 350 for forming the protective shell. In some embodiments, the mixture further includes a secondary drug 390. In some embodiments, the component 350 for forming the protective shell includes a component 351 for forming an outer layer of the protective shell, and a component 353 for forming an inner layer of the protective shell.

In some embodiments, the inner layer of the protective shell of the drug delivery system 300 is entirely formed by a shell portion of the component 370 for forming the linkage and, as such, no component 353 is need. In some embodiments, the inner layer of the protective shell of the drug delivery system 300 is formed by both the component 370 and the component 353.

Kit for Making Drug Delivery System

In some embodiments, the instant specification is directed to a kit for making a drug delivery system.

In some embodiments, the drug delivery system is the same as or similar to those as described above.

In some embodiments, the kit for making the drug delivery system includes a component for forming a lipid nanoparticle core. In some embodiment, the kit for making the drug delivery system further includes a component for forming a protective shell around the lipid nanoparticle core. In some embodiments, the kit for making the drug delivery system further includes a component for forming the linkage connecting the protective shell to the liposome core.

In some embodiments, the kit for making the drug delivery system further includes a primary drug suitable to be enclosed in the lipid nanoparticle core, a secondary drug suitable to be enclosed in a space between the lipid nanoparticle core and the protective shell, or both.

The method for making the drug delivery system from the kit is the same as or similar to those as described in the previous sections.

Method of Treating Cancer

In some embodiments, the instant specification is directed to a method of treating cancer.

In some embodiments, the instant specification is directed to a method of treating cancer using a drug delivery system the same as or similar to the drug delivery system as described above.

In some embodiments, the method of treating cancer includes administering to a subject in need thereof, the drug delivery system.

In some embodiments, the subject is a mammal. In some embodiments, the subject is a human.

In some embodiments, the cancer is a solid tumor cancer. In some embodiments, the cancer is breast cancer.

In some embodiments, the drug delivery system is administered to the subject intravenously.

EXAMPLES

The following Examples describe a process of making a drug delivery vehicle and a drug delivery system according to some embodiments.

The Examples further describe methods of treat cancer using the exemplary delivery vehicle and delivery system, as well as evaluation results including the efficacy and biocompatibilities.

Figure 8:
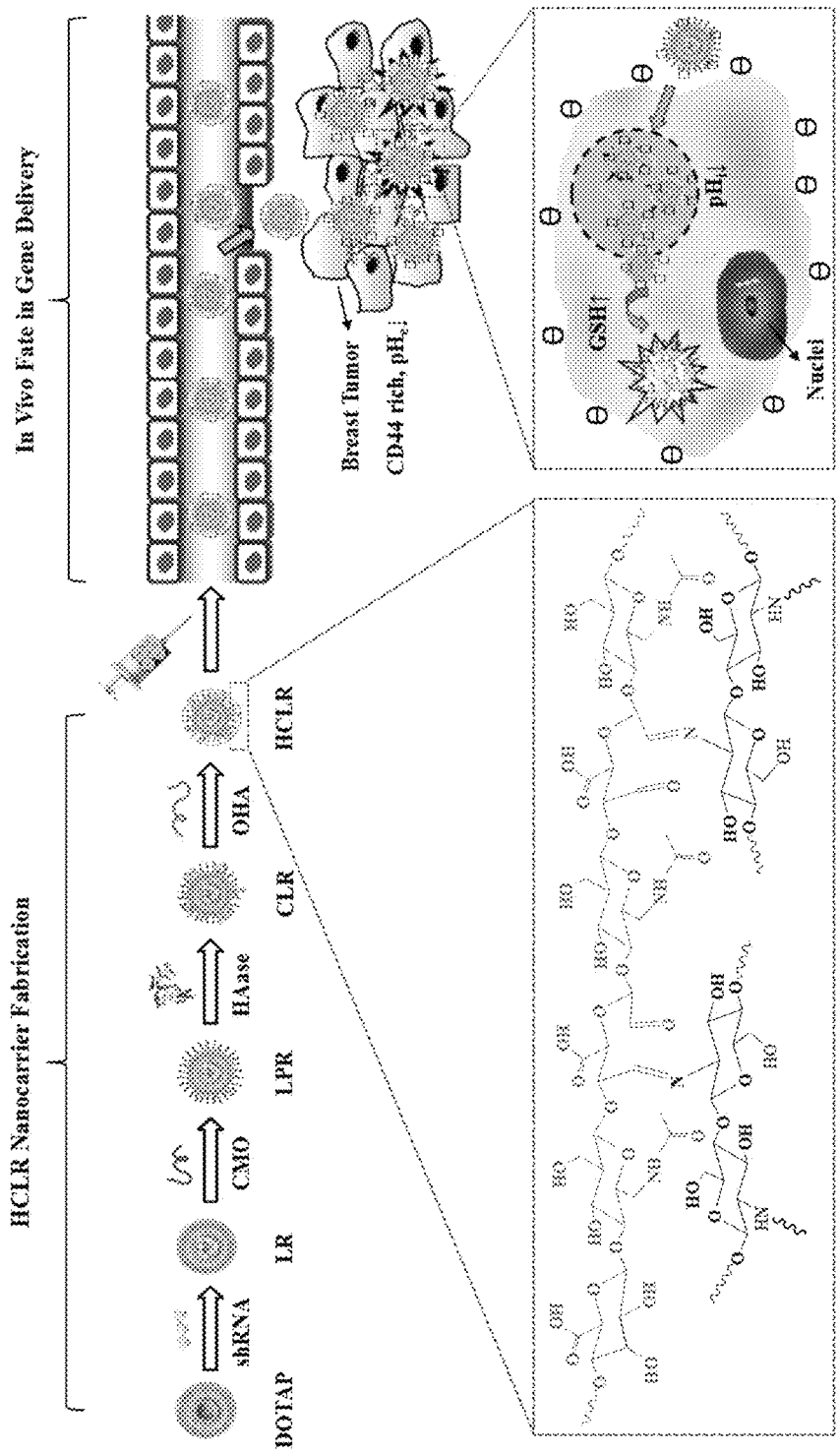
FIG. 8 is a process for making an exemplary drug delivery system and a method of treating a cancer using the exemplary drug delivery system in accordance with some embodiments.

Briefly, referring to FIG. 8, the exemplary drug delivery system is a stimuli-responsive polysaccharide enveloped liposome carrier, which was constructed by layer-by-layer depositing redox-sensitive amphiphilic chitosan (hereinafter "CS") and hyaluronic acid (hereinafter "HA") onto the dioleoyl-3-trimethylammonium propane (hereinafter "DOATP") liposome and then loading the inhibitor of apoptosis (hereinafter "IAP") inhibitor survivin-shRNA gene and permeation promoter hyaluronidase (hereinafter "HAase") sequentially. The as-prepared HA/HAase/CS/liposome/shRNA (hereinafter "HCLR") drug delivery system (also referred to as "nanocarrier" in the instant specification) was verified to be stable in blood circulation due to the negative charged HA shield. The tumor targeting recognition and the enhanced tumor accumulation of the HCLR were visualized by fluorescence resonance energy transfer (FRET) and in vivo fluorescence biodistribution. The deshielding of HA and the protonizing of CS in a slightly acidic tumor extracellular pH environment (pHe, 6.8~6.5) were demonstrated by zeta potential change from −23.1 mV to 29.9 mV. The pHe responsive HAase release was confirmed in the tumor extracellular mimicking environments, and the intratumoral biodistribution showed that the tumor penetration of HCLR was improved. The cell uptake of HCLR in pHe environment was significantly enhanced compared with that in physiological pH environment. The increased shRNA release of HCLR was approved in 10 mM glutathione (GSH) and tumor cells. Surprisingly, HCLR suppressed the tumor growth markedly through survivin silencing and meanwhile maintained low toxicity to mice. Without wishing to be limited by theory, the instant inventors believe that the results indicate that the novel polysaccharide enveloped HCLR is promising in clinical translation, thanks to the stimuli-triggered tumor accumulation, tumor penetration, cell uptake and intracellular gene release.

Example 1: Materials for Constructing the Exemplary Drug Delivery Vehicle and the Drug Delivery System Chitosan oligomer (CS, MW=1 kDa, acetylation degree <10%) was donated by Dalian Institute of Chemical Physics, Chinese Academy of Sciences, China). 2-Mercaptoethyl oleate (MO) was purchased from Micxy Reagent. N-Succinimidyl-3-(2-pyridyldithiol) propionate (SPDP), HA (MW=100 kDa), sodium periodate and dithiothreitol (DTT) were supplied by Aladdin Co. Ltd. (China). Dioleoyl-3-trimethylammonium propane (DOTAP) was obtained from Roche group. Branched polyethyleneimine (PEI, MW=25 kDa) was purchased from Sigma-Aldrich. HAase was supplied by Tokyo Chemical Industry. Human breast cancer cell lines of MDA-MB-231 & MCF-7 and mouse embryonic fibroblast cell line of NIH/3T3 were gifts from Prof. Zhen from Dalian Medical University. BALB/c nude mice were purchased from Model Animal Research Center of Nanjing University. Dulbecco's modified eagle's medium (DMEM) and trypsin were obtained from Gibco BRL (Gaithersburg, MD, USA). Fetal bovine serum (FBS) was purchased from Sijiqing Biologic Co., Ltd. (Hangzhou, China). DsRED fluorophore, survivin-shRNA (5'-AATTGAG-GAAACTGCGGAGA-3') with GFP as the reporter gene attached, GFP and CD44 fusion proteins were all purchased from Gene Pharma Co. Ltd. pGFP-N2 plasmids were amplified in *Escherichia coli* cells and used for particle size measurements and Gel retardation assays. Survivin (Invitrogen) and Bax (Proteintech) rabbit polyclonal antibody, HRP-labelled goat anti-rabbit IgG (H+L) (Proteintech), CoraLite594-labelled goat anti-rabbit IgG (H+L) (Proteintech) were purchased and used as received. All other biological reagents and assay kits were obtained from Beyotime Biotechnology or Elabscience Biotechnology.

Figure 9:
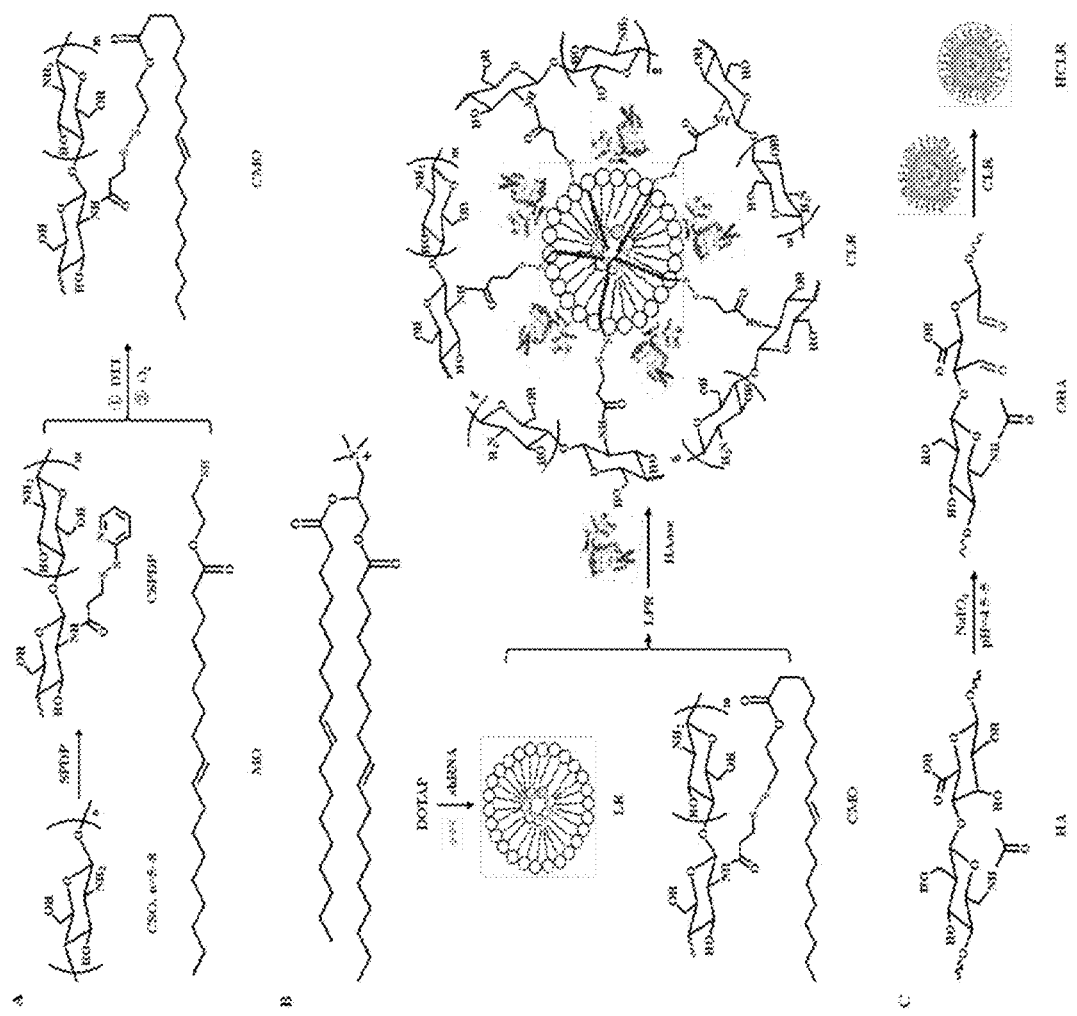
FIG. 9 is a process for making an exemplary drug delivery system in accordance with some embodiments.

Example 2: Methods of Constructing the Exemplary Drug Delivery Vehicle and the Drug Delivery System Referring to FIG. 9, to prepare the HCLR, CS modified with MO was firstly prepared to obtain hydrophobic oleic acid modified CS (hereinafter "CMO"). In a separate vessel 1 mg/mL DOTAP was mixed with 1 mg/mL survivin-shRNA at N/P ratio of 3:1 and incubated for 20 min at room temperature to form the lipoplex of DOTAP/survivin-shRNA (LR). Then CMO was deposited onto LR lipoplex to form chitosan-lipopolyplex (LPR, FIG. 1B) by adding 200 μL LR lipoplex into 600 μL CMO aqueous solution of 1 mg/mL and stirring at 700 rpm for 30 min. Then, excess CMO were removed by ultrafiltration tube with DI water (Millipore, 100 kD MW cutoff) for 2 min at 3000 rpm and 25° C. After cleaning with water, 100 μL HAase of 500 U/mL was incubated with LPR for 1 h at 25° C. to obtain HAase loaded LPR (CLR). Oxidized HA with oxidation degree of 5.9% ($OHA_{5.9}$) and 33.6% ($OHA_{33.6}$) was prepared from HA and sodium periodate. After removing excess HAase by ultrafiltration, 1% (w/w) 100 μL $OHA_{5.9}$ was added to CLR and sonicated for 2 min. After 15 min adsorption, the product was separated by ultrafiltration to remove the excess $OHA_{5.9}$. The HCLR nanocarrier was characterized by FTIR (Shimazu Prestige-21, Japan, potassium bromide pellet). The morphology and particle size were measured by transmission electron microscope (TEM, JEOL-2100, Japan), field emission scanning electron microscopy (FE-SEM Hitachi S-4800, Japan) and dynamic light scattering (DLS, MS-3000, England). The zeta potential was measured by electrophoretic light scattering on the DLS instrument. HLR was fabricated by the same procedure of HCLR.

Example 3: Methods of Evaluating Stability and Stimuli-Responsive Properties The physicochemical properties of the stability and the pH- and GSH-responsive shRNA release were investigated. After the nanocarriers were respectively diluted in DI water, 0.9% NaCl, PBS, PBS with 10% FBS (v/v), and DMEM with 10% FBS (v/v), the pH was adjusted to 7.4 and 6.5 with HCl or NaOH solutions. Then the time-dependent DLS measurement was performed to monitor the size variations of the nanocarriers during the period of 2880 min. To assess the stability in blood, HCLR nanocarrier and plasma (v/v=20%) were incubated at room temperature for 0, 5, 15, 30, 60, 90, 120, 240, 420, 720, 1440 min. Then the absorbance value at 450 nm was measured by ultraviolet spectrophotometer. Furthermore, the agorose gel electrophoresis (AGE) was performed after the nanocarriers were respectively incubated in 10 U/mL heparin and 10 U/mL heparin with 0.1 U/μL DNase I. The pHe-responsive HA deshielding of HCLR was evaluated by the zeta potential variation after incubated in PBS buffering with pH of 7.4 and 6.5 for 2 h. The stimuli-responsive HAase release from HCLR nanocarrier was investigated in different pH conditions. Briefly, according to the instructions provided with the Colorimetry Kit, the generation of glucosamine (GluA) with a new reducing N-acetyl-D-glucosamine terminus due to HAase degradation was quantitatively measured by each Morgan-Elson cleavage reaction. The proton buffering capacity was determined by an acid-base titration assay in the pH range from 10 to 3 to assess the lysosome escape ability. The gel electrophoresis of the nanocarrier was also used in 10 mM GSH to investigate the redox-responsive ability.

Example 4: Methods of Evaluating CD44 Targeting

The fluorescence resonance energy transfer (FRET) technique was used to measure the CD44 targeting ability of HCLR nanocarrier to MDA-MB-231 breast tumors. Specifically, MDA-MB-231 tumor cells were transfected by CD44/GFP fusion protein to express CD44 receptor labelled with a green fluorescent donor (supporting information). Replacing shRNA with DsRED as the red fluorescent acceptor, the HCLR nanocarrier was added to the GFP labelled MDA-MB-231 tumor cells and incubated for 0.5 h to localize the nanocarrier to the CD44 receptor. An Olympus FV-3000 confocal laser scanning microscope (hereinafter "CLSM") was used to observe the anchoring in 3.5 cm petridishes with a glass bottom (JingAn Bioligical, China). The FRET between the GFP tags localized at the cell CD44 receptors and the DsRED tags localized in the nanocarrier is investigated by observing the fluorescence emission between 517 nm and 582 nm using an excitation of 488 nm. For comparison, MCF-7 cells with lower CD44 receptor expression and NIH/3T3 cells with no CD44 receptor expression were also transfected with the CD44/GFP fusion protein, then followed by the FRET evaluation.

Example 5: Methods of Assaying Cell Uptake

Cell uptake was qualitatively and quantitatively evaluated by inverted fluorescence microscopy (Olympus IX71, Japan) and flow cytometry (Becton-Dickinson Accuri™ C6, USA). MDA-MB-231 cells were seeded in a 12 well plate until cell confluency achieved 80%. HCLR nanocarrier, labelled by Fluorescein isothiocyanate (FITC. $\lambda_{ex}$, 490 nm; $\kappa_{em}$, 520 nm) through reaction of amino with isothiocyanate, were added to the cultures and incubated for 4 h at 37° C. in a humidified 5% $CO_2$ incubator. The cells were then observed by an inverted fluorescence microscopy for qualitative evaluation after being washed with phosphate-buffered saline (PBS). For quantitative analysis by flow cytometry, cells were quenched by Trypan blue after PBS washing to remove the traces of the nanocarrier outside cells, then trypsinized and resuspended in PBS at a concentration of $1\times10^6$ cells/mL. To evaluate the HA deshielding and the CS charge reverse enhanced uptake of the HCLR nanocarrier, pH of the culture was adjusted to 6.5 and 7.4, respectively. HLR and LR nanocarrier uptakes were investigated as the comparative study. Furthermore, the uptake of HCLR in MCF-7 cells and NIH/3T3 cells was also respectively evaluated at pH 7.4 and pH 6.5.

Example 6: Methods of Estimating Endo/Lyso-Some Escape

To investigate the endo/lyso-some HCLR escape and cytoplasm shRNA release, cells at 80% confluence were incubated with FITC labelled HCLR at 37° C. in a humidified, 5% $CO_2$ incubator in 3.5 cm petridishes with glass bottoms. After incubated in cultures of pH 6.5 for 4 h, cells were washed with PBS and then sequentially incubated with Lyso-Tracker Red ($\kappa_{ex}$, 577 nm; $\kappa_{em}$, 590 nm) for 10 min to visualize the late endo/lyso-somes. After five washings with PBS, cells were observed under CLSM and analyzed with FV10-Viewer software (Olympus, Tokyo, Japan) to track the intracellular endo/lyso-some escape of HCLR nanocarrier. HLR and LR nanocarriers were investigated as the comparative study.

Example 7: Methods of Evaluating In Vitro shRNA Delivery and Inhibition of Proliferation MDA-MB-231 cells were seeded in 24-well plates for approximately 18-24 h before experiments commenced. HCLR nanocarrier was added to the cells and incubated in DMEM of pH 6.5 for 4 h at 37° C. Media was replaced with DMEM containing 10% FBS and 1% antibiotics. After incubation for another 48 h, the cells were examined by inverted fluorescence microscopy to observe the green fluorescence intensity distribution to see where GFP expression peaked and estimate the efficacy of gene delivery. Flow cytometry was also used to quantify the transfection efficiency. HLR and LR nanocarriers were investigated as the comparative study.

The measurement of inhibition to cell proliferation was estimated using the cell counting assay (CCK-8). Briefly, HCLR, HLR and LR nanocarriers at the same level of shRNA incorporation (0.5 μg per well) were incubated in 96-well plates at a density of 5,000 cells per well. After a transfection period of 48 h, the cell proliferation assay was performed in accordance with kit instructions. The optical density (OD) at 450 nm was read by a multimode microplate reader (SynergyH1, Biotek, USA) in three duplicate samples. The proliferation of cells was analyzed according to the OD value of each well, with the proliferating percentage of cells calculated by the formula: (%)=($OD_{sample}$−$OD_{blank}$)/($OD_{control}$−$OD_{blank}$)×100%. Meanwhile, shRNA was replaced with a negative control of shNC (5'-TAT-GAGAATGGCAGCGAGATA-3') to form the corresponding negative control groups. The efficiency of inhibition by negative control nanocarriers was also estimated as the comparative study to further certify the significance of HCLR, HLR and LR nanocarriers.

Immunofluorescence (IF) was also used to evaluate inhibition efficiency caused by HCLR nanocarriers. After 48 h of transfection with HCLR nanocarriers, cells were fixed with 4% parformaldehyde (PFA) and washed 3 times with PBS. Normal goat serum was added and incubated for 20 min to block non-specific sites. Diluted survivin rabbit polyclonal primary antibody was added and incubated at 4° C. overnight. Diluted CoraLite594 conjugated goat anti-rabbit IgG (H+L) was then added as secondary tagged antibody and incubated for another 15 min. After nuclei were stained with DAPI, the cells were rinsed with PBS three times and sealed with neutral resin, then observed by CLSM. The quantitative silencing efficacy was derived from the counting statistics method by using IPWin60C software.

Example 8: Methods of Evaluating In Vivo Biodistribution

In vivo studies were carried out on BALB/c nude mice 4-6 weeks of age in which tumors were established by subcutaneously inoculating $1.0 \times 10^7$ MDA-MB-231 cells into the right armpit of the mice. All experiments performed on the animals were approved by the Institutional Animal Care and Use Committee at Dalian Medical University. When the volume of the tumor increased to about 100 $mm^3$, HCLR, HLR and LR nanocarriers were administered by tail vein injection (20 µg survivin-shRNA per mouse) with 5 mice for each group, using saline as control.

To measure the in vivo biodistribution of the nanocarriers, the instant inventor tagged the nanocarriers with 1% DiR and administered them to mice by injection in the caudal vein. Blood samples were harvested by eyeball blood collection at 0, 0.5, 1, 2, 4, 8, 12, and 24 h after the treatment. After extracted with ethyl acetate for 3 times to collect DiR, the blood samples were analyzed by fluorescence spectrometer. The mice were examined by fluorescent optical imaging during 24 h after injection, using an in vivo fluorescence imaging system (In-Vivo FX PRO, Canada) with Carestream MI SE software. Then the mice were sacrificed, and the major organs (heart, liver, spleen, lung, and kidney) were collected to be fluorescently imaged. To evaluate the intratumoral distribution of the nanocarriers, the whole cross sections of the tumors were examined by CLSM.

Example 9: Methods of Evaluating In Vivo Gene Silencing and Anti-Proliferation To evaluate the long-term effectiveness of gene transfection, another group of mice were administrated with the nanocarriers. Tumor sizes were recorded during 20 days of post-injection to evaluate the effectiveness of survivin silencing therapy and the tumor proliferation inhibition. After 20 days, the mice were sacrificed to harvest the tumors and the major organs. All tissues were washed 3 times, fixed in 4% PBS buffered paraformaldehyde, embedded in paraffin wax, and sliced into optical sections.

Immunohistochemistry (IHC) staining was performed for survivin and Bax protein expression analyses, using antibody concentrations recommended in the manufactures' instructions. Briefly, exposure to 0.5% triton-X100 for 30 min at room temperature was employed to increase permeability of the tissue slices before being washed out with PBS. Goat serum, the homologous serum of the secondary antibody, was applied to the tissue slices for 15 min. The primary rabbit polyclonal antibody specific to survivin or Bax was diluted in PBS (in the proportion of 1:50 v/v) and incubated with the tissue slices at 4° C. overnight. After 3× rinsing in PBS, the slices were incubated with the secondary antibody of HRP-labelled goat anti-rabbit IgG (H+L) for 10 mins at room temperature. Final staining resulted by addition of 3,3'-diaminobenzidine (DAB) and observed by microscopy (Olympus IX71, Japan).

The apoptosis analysis was carried out by terminal deoxynucleotidyl transferase-dUTP nick end labeling (TUNEL) method, following the manufactures' instructions. Briefly, after washing with 0.85% NaCl and PBS, the tissue section was fixed with 4% paraformaldehyde for 15 mins. Sections were then covered with Proteinase K solution for 8-10 mins and equilibrium buffer for an additional 5-10 mins before addition of the TdT reaction mixture. After incubation under dark conditions for 1 h, the sections were incubated with saline sodium citrate (SSC) solution for 15 min and followed by a PBS wash. Each section was then examined and photographed with a fluorescence microscope (Olympus IX71, Japan). Tumor tissues were also analyzed by histological examination using hematoxylin and eosin (H&E) staining to catalog cancer cell proliferation.

Example 10: Methods of Evaluating Biocompatibility

The time variation of mice's body weight was recorded to determine the systemic toxicity of the nanocarriers. At autopsy, blood was collected in heparinized test tubes from neck vessels and centrifuged at 3,000 rpm for 20 min to obtain plasma. To determine liver and kidney toxicity, plasma samples were used to estimate the activity of alanine aminotransferase (ALT) and aspartate aminotransferase (AST), and to quantify total bilirubin (TB), creatinine (CREA), serum urea nitrogen (SUN), and cysteine protease inhibitor C (Cys-C) by ELISA. The paraffin-embedded sections of major organs, such as the heart, liver, spleen, lung and kidney, were stained by H&E and then observed by optical microscopy to investigate the biocompatibility of the nanocarriers in these organs.

Example 11: Methods for Statistical Analysis

Statistical analysis between the control and survivin silenced groups was carried out using two-way analysis of variance. Mean value and the standard deviation (mean±SD) of the data were calculated. The differences were determined by one way ANOVA analysis and considered to be statistically significant if $P<0.05$.

Figure 10:
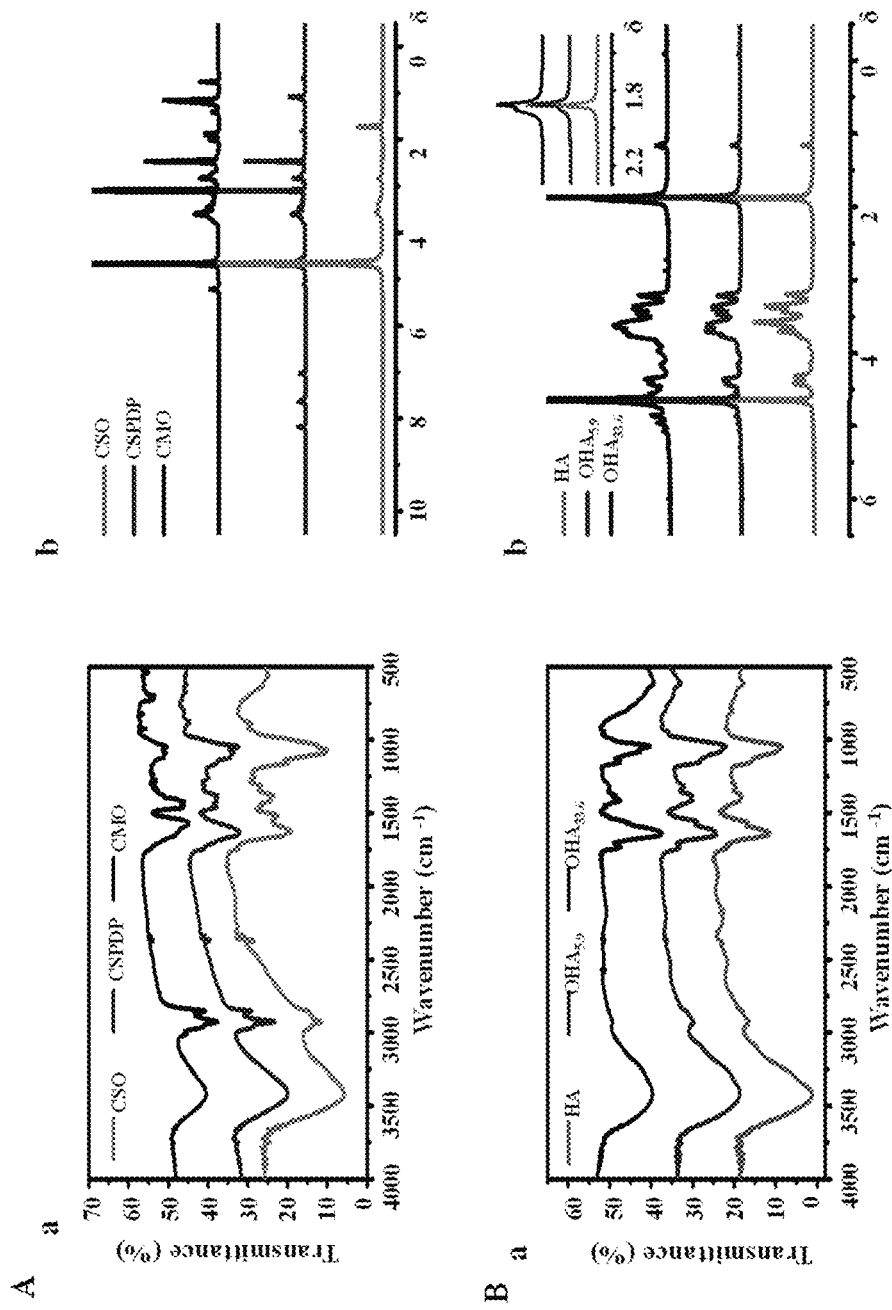
FIG. 10 is graphs of characterization results of components used in making an exemplary drug delivery system in accordance with some embodiments.

Example 12: Method of Synthesis HCLR Nanocarriers and Characterization of HCLR Nanocarriers To modify CS onto the liposome periphery, GSH-responsive CS derivative of CMO with a hydrophobic oleic acid tail was synthesized. Specifically, chitosan with an oleic acid tail (CMO) was synthesized from the chitosan oligomer (CS, MW=1 kDa, acetylation degree <10%) and 2-mercaptoethyl oleate (MO). CS and N-succinimidyl-3-(2-pyridyldithiol) propionate (SPDP) at a molar ratio of 1:1 reacted under stirring in $H_2O$/DMSO (V/V=10:1) solvent at room temperature for 2 h. Twenty mM DTT was added to reduce pyridyldithiol for 12 h under Na atmosphere followed by reacting with MO under an O2 atmosphere for another 12 h to produce CMO. After dialysis and lyophilization against water, CMO was obtained as a pale power. Referring to FIG. 10, the successful synthesis of CMO was confirmed by using FTIR (Shimazu Prestige-21, Japan, potassium bromide pellet) and $^1$HNMR (Varian Mercury plus400, USA, $D_2O$). The new peaks at δ 5.2, δ 1.2 and δ 0.8 in $^1$HNMR spectra (FIG. 11, panel A-a) and the increased peaks at 2925 $cm^{-1}$ and 1576 $cm^{-1}$ in FTIR spectra (FIG. 11, panel A-b) demonstrated the successful synthesis of CMO. Then CMO was post-inserted into LR and loaded with HAase. Characterization of chitosan derivatives is also shown in FIG. 10, panel A. The new peaks at 1454 $cm^{-1}$ in FTIR spectra and δ 7.0~8.2 in $^1$HNMR spectra (aromatic ring) demonstrated the successful synthesis of CSPDP after SPDP modification. The increased peaks at 2925 $cm^{-1}$ and 1576 $cm^{-1}$ in FTIR spectra, the disappeared aromatic ring peak and the new peaks at δ 5.2, δ 1.2 and δ 0.8 in $^1$HNMR spectra demonstrated the successful synthesis of CMO after DTT reduction and $O_2$ oxidation.

After HA was slightly oxidized by sodium periodate, the product $OHA_{5.9}$ with a low oxidization degree was used to block the nanocarrier surface through a mild ionic and chemical cross-linking method. Specifically, oxidized HA (OHA) was prepared from hyaluronic acid (HA, MW=100 kDa) and sodium periodate. Briefly, degassed HA and sodium periodate solution were mixed and reacted at 0-4° C. for a period of time, then the solution was dialyzed and lyophilized to obtain OHA. By varying the oxidization conditions, OHA products with different oxidation levels were obtained and characterized by FTIR (Shimazu Prestige-21, Japan, potassium bromide pellet) and $^1$HNMR (Varian Mercury plus400, USA, $D_2O$). $OHA_{5.9}$ ensured that the majority of the aldehyde groups were consumed, which weakened the interaction of HCLR and the blood components to benefit the long circulation. Also referring to FIG. 10, panel B, the HA derivatives were characterized by FTIR and $^1$HNMR. The new peak at approximately 1720 $cm^{-1}$ in FTIR spectra and the new peaks at about δ 4.9~5.1 in $^1$HNMR spectra were the aldehyde group peak of OHA. The aldehyde peaks at δ 4.9 to δ 5.1 were calculated to represent 5.9% and 33.6% conversion of the galactose for $OHA_{5.9}$ and $OHA_{33.6}$, with the peak at δ 1.8 as the internal standard. The intensity of the new peaks of $OHA_{33.6}$ was significantly stronger than that of $OHA_{5.9}$ due to the higher oxidation degree of $OHA_{33.6}$. The characteristic affiliation peak in OHA $^1$HNMR spectra originated from the formation of aldehyde group. Furthermore, the shift of —$CH_3$ in amide groups (at about δ 1.8) to low-field NMR also demonstrated the success synthesis of OHA.

Figure 11:
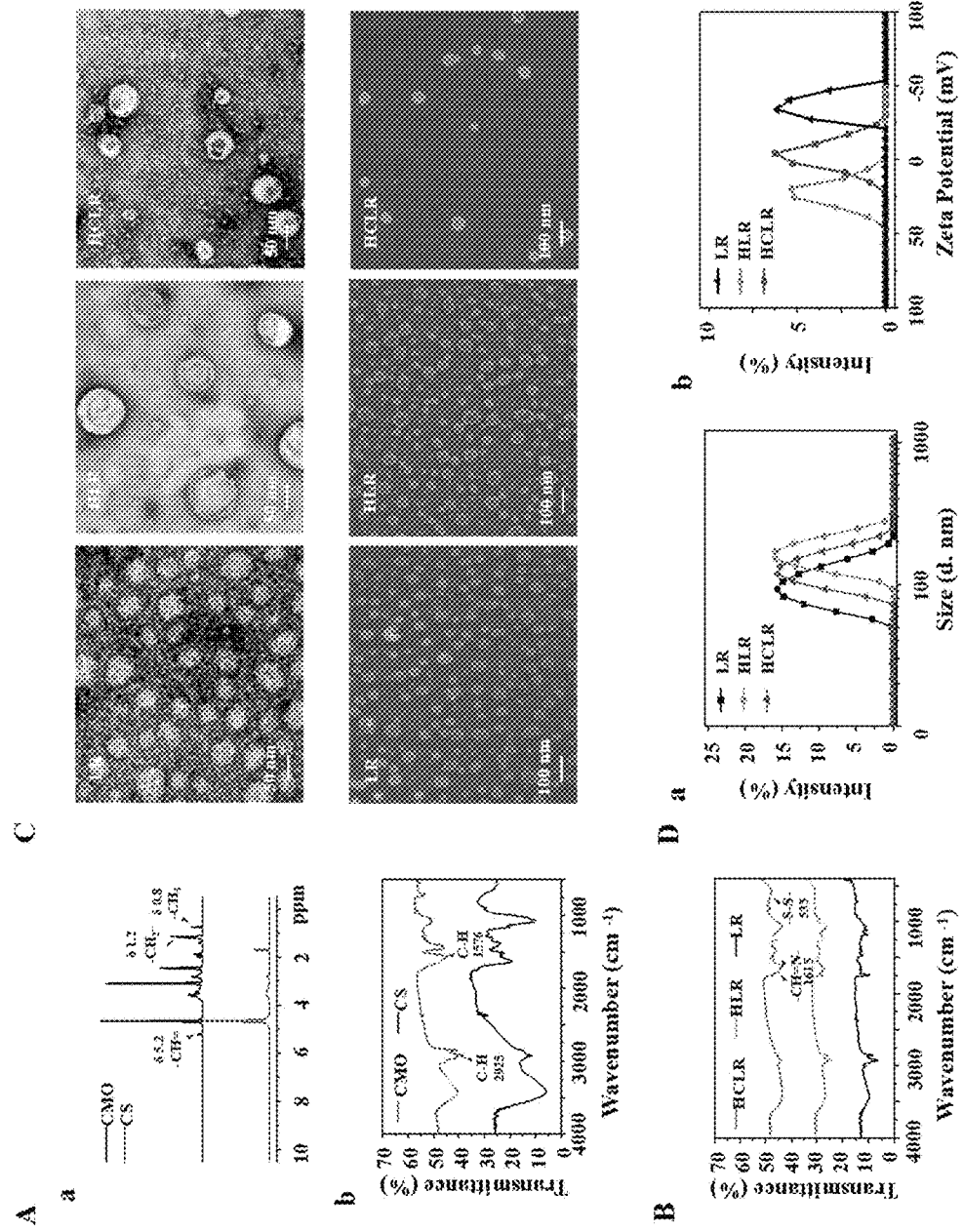
FIG. 11 is graphs and images of characterization results of an exemplary drug delivery system in accordance with some embodiments.

The FTIR spectrum of the HCLR nanocarrier was shown in FIG. 11, panel B. Compared with LR and HLR, the slight peak enhancement observed at 1615-1683 $cm^{-1}$ can be attributed to the Schiff base linkage (—CH═N—) in HCLR formed by OHA and CS reaction. Moreover, the increase of the weak broad peak in the spectra of HCLR at 539 $cm^{-1}$ illustrated the disulfide structure of CMO.

The morphology, size and zeta potential of the nanocarriers were measured by TEM, SEM and DLS (FIG. 11, panels C and D). The TEM and SEM results showed that LR, HLR and HCLR were nearly spherical particles. The average size of HLR increased to 90~100 nm in TEM images after HAase loading and HA modification, compared with that of LR (ca. 50 nm in TEM images). However, the diameter of HCLR was decreased to ca. 70 nm after layer-by-layer modification of CMO and HA. The DLS results also showed that the hydration sizes of HLR and HCLR were 162.3±5.2 nm and 105.1±6.7 nm, and the corresponding polydispersity index (PDI) were 0.174±0.033 and 0.118±0.028, respectively. Without wishing to be bound by theories, the instant inventors hypothesized that the chemical and ionic cross-linking of $OHA_{5.9}$ and CMO induced a more compact structure of HCLR. In contrast, HLR with just mild ionic cross-linking between HA and DOTAP presented a looser structure. The zeta potentials of LR, HLR and HCLR were measured to be 33.9 mV, −20.2 mV and 3.5 mV, respectively. The nanocarriers with hydration sizes of ca. 100~200 nm and negative or neutral surface charge have the advantage of decreasing elimination and extending blood circulation. So HCLR would be suitable for tumor targeting delivery.

Figure 13:
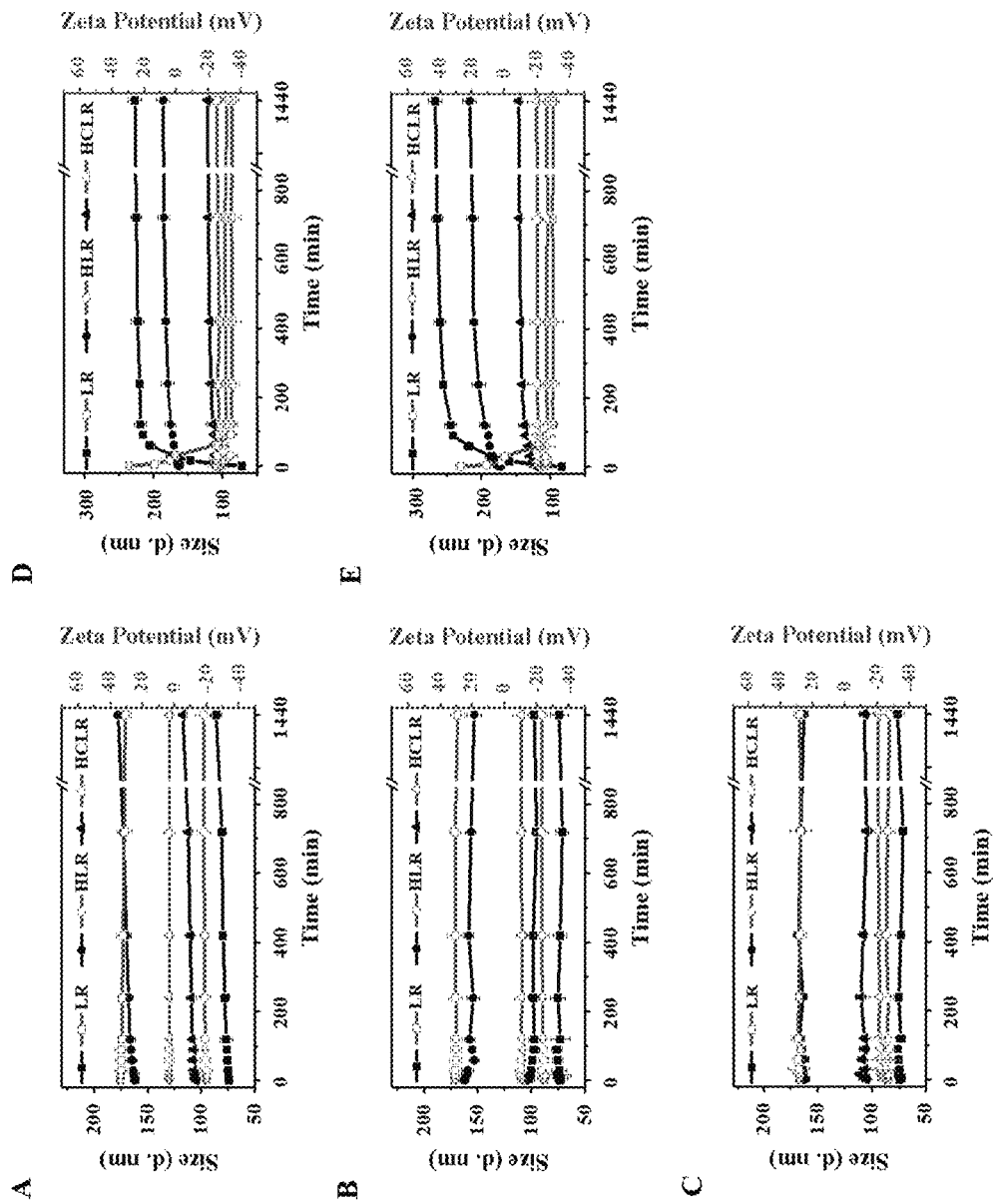
FIG. 13 is graphs of time-dependent size and zeta potential variations of an exemplary drug delivery vehicle in accordance with some embodiments.

Example 13: Results of the HCLR Nanocarriers Stability, pH- and GSH-Responsiveness Studies The stability under physiological conditions and the following stimuli-responsive sequential payload release are beneficial for a nanocarrier to accomplish the tumor targeting delivery. The time-dependent DLS measurement was performed to monitor the size variations of the nanocarriers in DI water, 0.9% NaCl, PBS, PBS with 10% FBS (v/v), and DMEM with 10% FBS (v/v) of pH 7.4 (FIG. 12, Panel A and FIG. 13). The sizes of HCLR and HLR did not change obviously during 2880 min, which indicated the nanocarriers were stable in a neutral physiological environment. Referring to FIG. 12, Panel B, after adding plasma into the nanocarriers, the absorbance of LR increased immediately due to the increased agglomerate, but that of HA modified HLR and HCLR did not increase. The results indicated the negatively charged surface of HLR and HCLR weakened the interaction between the nanocarrier and the plasma protein, which enhanced the circulation stability. The circulation stability of HCLR was also tested in a blood mimicking solution of 0.1 U/μL DNase I and 10 U/mL heparin. As shown in FIG. 12, panel C, there was little gene degradation or gene release of HLR and HCLR in the mimicking solution, indicating the HA modification stabilized HCLR in blood circulation. However, the LR lipoplex did not survive against nuclease degradation and was susceptible to dissociation in the competitive adsorption by the negatively charged macromolecules in blood.

The size variation of HCLR at pH 6.5 was also measured by DLS to monitor the pH-response of the nanocarrier (FIG. 12, panel A). The results showed that the size of HCLR increased obviously at pH 6.5 after 30 min compared with that of HLR and LR. This could be ascribed to the pH-responsive ability of HCLR, which caused the swelling of the envelope. The size of HCLR decreased to ca. 136 nm and remained stable after 60 min, which indicated the envelope deshielding and the size decreasing. The results suggested that HCLR could respond to the pHe of the tumor microenvironment. The deshielding of HA and sequential HAase release in tumor site was further investigated by measuring the variations of the surface charge and the HAase enzymatic activity in pHe environment. Compared to the negative zeta potential of HCLR nanoparticle at pH 7.4, an increase of zeta potential to 27.8 mV was observed under pH 6.5 after incubating for 2 h (FIG. 12, panel D), suggesting the pH-responsive deshielding of HCLR. The change of the zeta potential from negative to positive also helped to facilitate the cell uptake. Furthermore, the increase of GluA content was observed when HCLR was incubated in pH 6.5 environment for 2 h (FIG. 12, panel E), illustrating the successful pH-responsive release of HAase from HCLR. However, the change of GluA content in HLR with the pH was not evident. The results of Morgan-Elson method demonstrated the enzyme activity was blocked in pH 7.4 after being formulated into HCLR nanocarrier and largely recovered in pH 6.5, while the enzyme activity of HLR was not observed either in pH 7.4 or in pH 6.5. Such acidic pH responsive release of HAase from HCLR would enable specific degradation of tumor-associated HA instead of nonspecific degradation of HA existing in normal connective tissues.

The proton buffering capacity of the gene delivery system is beneficial for the endo/lyso-some escape. The titration curves were shown in FIG. 12, panel F-a. The buffering capacities of HCLR, HLR and LR were 21.6%, 14.6% and 9.75%, respectively. The results demonstrated that the buffering capacity of HCLR was significantly improved after CS modification, which would cause a faster endosomal escape. The pH derivative sketch also clarified the buffering capacity apparently (FIG. 12, panel F-b). The valley of HCLR curve appeared at ca. pH 6.5, indicating the strong proton buffering capacity at the pH value. In addition to cellular pH response, glutathione (GSH) is a cellular constituent for triggering controlled release of the silencing gene from its delivery vehicle. Normally, the concentration of GSH in tumor cells can be as high as 10 mM. The instant inventors therefore measured the stability of HCLR and its redox-responsive gene release in a GSH concentration of 10 mM by AGE. The results showed that HCLR was prone to gene release under these reducing conditions (FIG. 12, panel G). However, LR and HLR remained stable under the same condition. It is well known that intracellular reduction of disulfide groups can be exceedingly fast in the presence of high GSH concentrations (approximately 2-10 mM in the cytosol). Therefore, the instant inventors surmise that HCLR containing disulfide groups will be stable in the extracellular environment, but can be induced to release their gene cargoes once they are endocytosed and enter the cytosol.

Example 14: Results of the CD44 Targeting Ability Studies

Tumor accumulation and tumor penetration are barriers in tumor targeting delivery. Active targeting and passive targeting both benefit the tumor accumulation. The enhanced permeability and retention (EPR) effect of a nanocarrier promotes the tumor accumulation through passive targeting. The active targeting ability of the HCLR nanocarrier to MDA-MB-231 tumor cell by CD44 receptor recognition was directly visualized by FRET technique. GFP and DsRED were served as donor and acceptor fluorophores. Results indicate that within the localized radiation field of the red acceptor dye, the fluorescence intensity at the 517 nm GFP (green) emission line, generated by exciting GFP sites with blue (488 nm) light decreased, while the intensity at the 582 nm (red) emission line of DsRED increased. The observed FRET phenomenon showed that the distance between the donor and the acceptor was within 10 nm for dipole mediated energy transfer. This implied that the HCLR nanocarrier localized to a binding site (the CD44 receptor) close enough for energy to be exchanged between the fluorophores. However, no FRET effects were observed in cells incubated with LR nanocarriers, which was the same result found for the control group (cells only). MCF-7 cells with lower CD44 receptor expression and NIH/3T3 cells with no CD44 receptor expression were also investigated as the comparative study. The FRET signal was weak in HCLR treated MCF-7 cells and no FRET phenomenon was observed in HCLR treated NIH/3T3 cells. These results demonstrated that the HCLR nanocarrier measurably targeted the CD44 receptor.

Example 15: Results of the HCLR In Vitro shRNA Delivery and Anti-Proliferative Activity Studies The instant inventors evaluated shRNA delivery of HCLR and HLR in vitro by measuring the GFP expression in MDA-MB-231 breast cancer cells using the fluorescence microscopy and flow cytometry (FIG. 15). Referring to FIG. 15, panel A, the GFP gene loaded in HCLR was expressed at higher intensity than the expression of the same gene carried by the HLR and the LR nanocarriers. The counting statistics results by IPWin60C demonstrated that the fluorescent intensity of GFP in HCLR group was ca. 43.6% and 58.4% higher than that of HLR group and LR group, respectively. Flow cytometry further showed that the HCLR nanocarrier produced >1.4-fold increase in the transfection efficiency over HLR and LR (FIG. 15, panel B). The increase was attributed to the enhanced cell uptake and endo/lyso-some escape as shown in FIG. 15, panels B and C, thanks to the charge reverse and proton buffering from CS modification. The results suggested that the HCLR nanocarrier delivered genes in a more efficient way to achieve effective gene expression.

The instant inventors examined the HCLR nanocarrier's in vitro anti-proliferation efficacy by using a tetrazolium salt viability assay (CCK-8) with negative control nanocarrier (by replacing shRNA with negative control shNC). The results in FIG. 15, panel C showed that the viability of cells treated with HCLR decreased to 63% (values were normalized to those obtained from untreated control cells, set as 100% viability), lower than that of HLR (81%) and LR (66.3%). The negative control groups of HCLR and HLR both exhibited cell viability >95%, which also demonstrated the biocompatibility of HCLR. The difference of cell viability in shRNA and shNC groups may be attributed to the anti-proliferation capability of shRNA. The results demonstrated that the HCLR nanocarrier was efficient for anti-proliferation, compared with their non pH-responsive HA deshielding counterpart HLR. The results of survivin immunofluorescence (IF) analysis further demonstrated a reduction in red fluorescence in cells treated with HCLR, HLR and LR as compared with the negative control groups (FIG. 15, panel D). Moreover, HCLR treated cells presented very small amount of red fluorescence and the silencing efficiency reached 72.5%, surpassing that of HLR (54.8%) and LR (48.6%). The results indicated a specific survivin expressing inhibition of HCLR was obtained through efficient shRNA delivery. Survivin is a member of the inhibitor of apoptosis (IAP) family of proteins, so the silencing of survivin could result in increase of apoptosis, decrease of tumor growth and expected anti-proliferation.

Example 16: Results of the In Vivo Biodistribution, Tumor Accumulation and Penetration Studies The in vivo biodistribution of the nanocarrier was also carried out to evaluate the effect of the CD44 targeting on the tumor accumulation. The half-life time of the HLR and the HCLR nanocarriers was longer than 8 h (FIG. 16, panel A). After 24 h post-injection, the dose decreased to the level of the saline control group. The time-dependent whole body fluorescence imaging results showed that the tumor accumulation of HCLR group was significantly increased with the time, and was higher than that of HLR group after 24 h (FIG. 16, panel B). The result was also demonstrated by the tumor fluorescence images (FIG. 16, panel C). However, LR groups exhibited little fluorescence in the tumors. The enhanced tumor accumulation of HCLR was suggested to be attributed to the active CD44 targeting ability. In the case of the LR nanocarrier, the cationic liposome has been shown to interact with anionic components in the blood plasma that accelerated the clearance rate and lowered the circulation time. LR accumulated in the tumor mainly by passive targeting mostly due to the EPR effects, and the short half-life time of LR resulted in the poor accumulation.

The accumulation of the nanocarriers in tumor tissue is beneficial. Nevertheless, the subsequent penetration in tumors is also beneficial to achieve high efficacy. To directly observe the penetration of the HCLR nanocarriers in tumor, the whole cross sections of tumors were observed on CLSM to investigate the penetration of HCLR through labelled DiR. More detailed distribution of the nanocarriers in tumor could be found in FIG. 16, panel D. For HLR and LR, the fluorescence was found to mainly distribute in the peripheral region of tumor tissue where a rich vascular network could be found. In contrast to this, much more fluorescence could be found in the deep region of HCLR treated tumor, indicating the excellent tumor penetration ability. The pHe responsive HAase release, which decreased the density of the extracellular matrix (ECM) and accelerated the diffusion the nanocarrier in tumor, was suggested to be responsible for the better tumor penetration ability. Moreover, compared with HLR and HCLR, weaker fluorescence could be found near the peripheral region for LR. This phenomenon was in good agreement with the weaker retention ability of LR in FIG. 16, panels B and C.

Example 17: Results of the HCLR In Vivo Anti-Tumor Activity Studies

Figure 17:
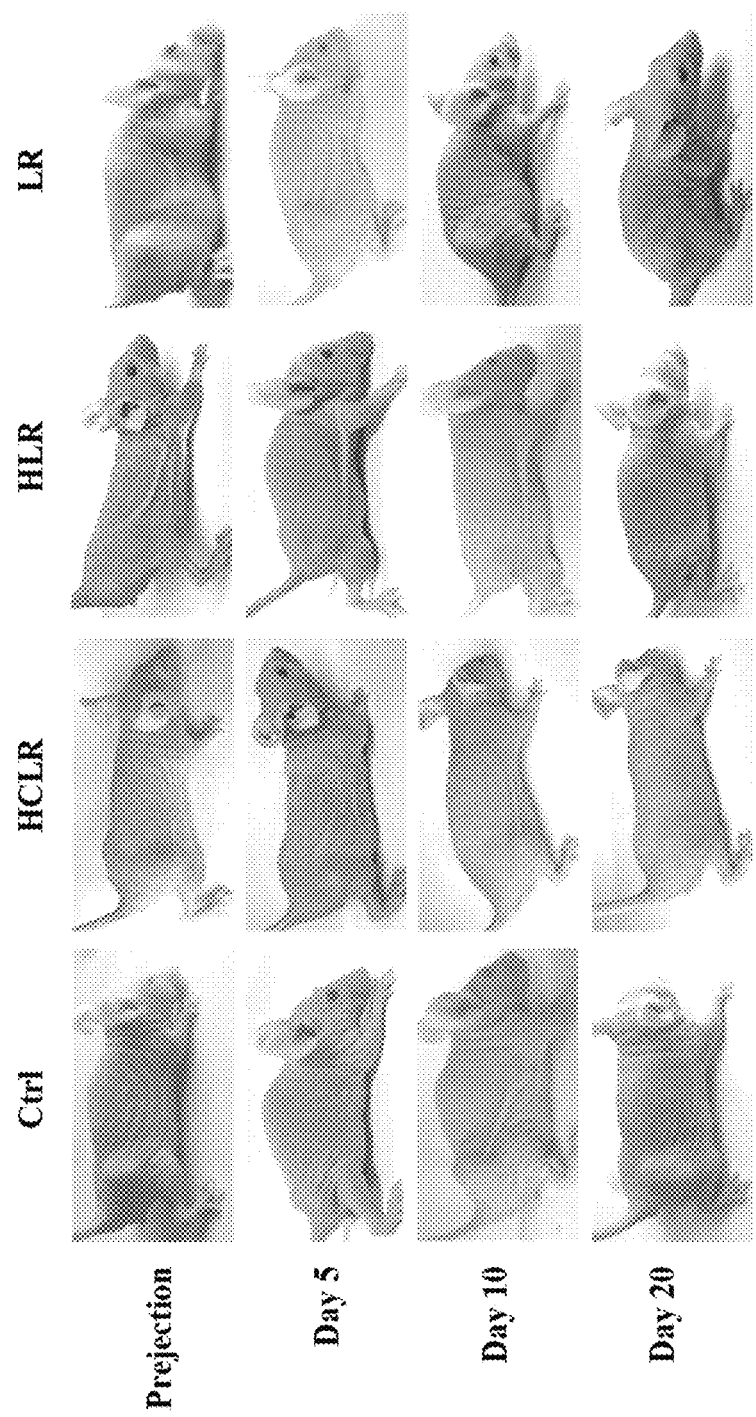

To evaluate the anti-tumor efficacy of HCLR in vivo, the tumor volumes were recorded in 20 days as shown in FIG. 16, panel E. The photographs of the mice in the course of the different treatment time points were taken (FIG. 17). The tumors were also collected after 20 days post-injection (FIG. 16, panel F). All the results demonstrated that the tumor growth in mice treated with HCLR was significantly inhibited compared with other groups. Tumor size in the HLR group was nearly 2× larger while tumor size in LR and saline groups were nearly 4× larger. Rated by the metric of tumor volume, the HCLR nanocarrier exhibited superior tumor suppression capability. As discussed previously, the outstanding anti-proliferation activity of HCLR may be attributed to its controlled gene transduction capacity, such as blood circulation stability, excellent tumor accumulation and tumor penetration, rapid endo/lyso-some escape within tumor cells and significant conversion by Dicer to inhibitory RNA products for the desired gene silencing.

Immunohistochemistry (IHC) was carried out to compare effects of direct gene silencing by HCLR and other carriers in vivo by measuring survivin and Bax protein expression (FIG. 16, panel G). The results showed that survivin protein expression was significantly lower in tumor tissues of HCLR and HLR groups than that in the saline control and LR groups. Survivin protein was demonstrated to be crucial for tumor genesis, proliferation, and metastasis. Down-regulation of survivin protein has been shown to induce apoptosis, suppress proliferation, and promote metastasis of tumors. The pro-apoptotic protein Bax is generally up-regulated during apoptosis. The instant inventors observed that Bax protein expression was significantly higher in HCLR and HLR groups, compared with the saline control and LR groups (FIG. 16, panel G). More surprisingly, the expression of Bax protein in the HCLR group was most evident. Bax protein was negatively correlated with expression of survivin protein, and silencing RNA to down-regulate survivin protein would up-regulate Bax protein. The IHC images of survivin and Bax demonstrated that HCLR nanocarriers effectively delivered shRNA into tumors and produced survivin gene silencing with increased apoptosis, leading to inhibition of tumor growth.

TUNEL and H&E analysis of tumor tissue slices were also used to investigate the anti-proliferation efficiency of HCLR nanocarriers. Compared with the other groups, greater green fluorescence in TUNEL staining and light pink color (extracellular matrix) in H&E staining were observed in the HCLR group (FIG. 16, panel G). The results showed that there were additional DNA fragments, condensed nuclei, and greater cytoplasmic shrinkage in HCLR group that are typical characteristics of apoptotic cells. These results were consistent with IHC results and further characterized the effectual anti-proliferation of HCLR nanocarriers in treating tumors.

Example 18: Results of the In Vivo HCLR Biocompatibility Evaluations

Figure 18:
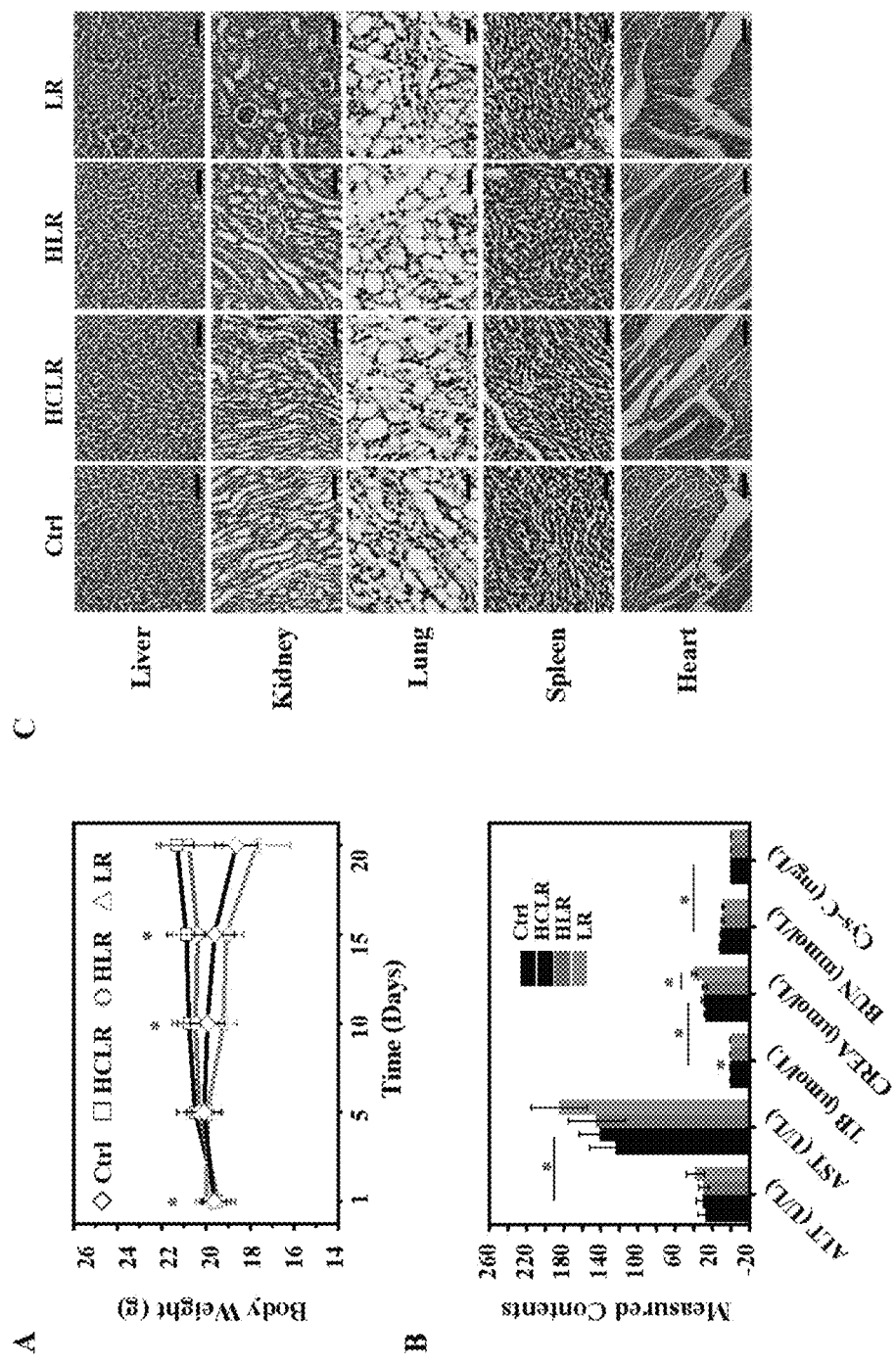
FIG. 18 is images and graphs of biocompatibility evaluation results of a drug delivery system according to some embodiments.

The biocompatibility of a gene delivery system is critical for the success of potential clinical applications. The instant inventors evaluated the biocompatibility of HCLR nanocarriers by the body weight measurements during 20 days post-presentation of survivin silencing therapy (FIG. 18, panel A). Average body weights of HCLR and HLR groups showed increases of 9.7% and 6.7%, respectively. However, body weights of the saline group showed a decrease of 5.1% in 20 days as a result of increased metabolic demand from the implanted MDA-MB-231 xenograft tumor. Body weights of the LR group decreased more than the saline group, most probably due to the toxicity of LR to cells and tissues as well as increased metabolic demands imposed by the tumor. The body weight variation demonstrated the biocompatibility of HCLR nanocarrier and its superior anti-proliferation capability, which suppressed tumor growth and reduced the metabolic demand of tumors bearing on mice.

After mice were sacrificed, serum ALT, AST, TB, CREA, BUN and Cys-c were examined by ELISA to determine the systemic toxicity of each treatment at the applied doses. The results in FIG. 18, panel B showed that ALT, AST, TB, CREA, BUN and Cys-c measurements in HCLR and HLR groups were all comparable to the saline group (Ctrl) that indicated low hepato-renal toxicity and good biocompatibility of these nanocarriers. However, ALT, AST and TB etc. measurements in the LR group significantly departed from normal levels, indicating systemic toxicity of LR. In addition, histological analysis of organs inspected by H&E staining generally confirmed these findings (FIG. 18, panel C). The major organs, such as liver, kidney, lung, spleen and heart, of the mice treated with HCLR and HLR did not show visible damage when compared with the saline group (Ctrl). However, the histology sections of liver, kidney and spleen in the LR group showed toxic pathologies such as structural disorder and hemorrhage (FIG. 18, panel C). Overall, our study found that HA and CS modified gene silencing nanocarriers had low toxicity and good tumor selectivity, suggesting that HCLR-like formulations should be a promising path for further development of gene delivery vehicles in many clinical applications.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A drug delivery vehicle, comprising:
a lipid nanoparticle core, wherein the lipid nanoparticle core is configured to enclose a primary drug;
a protective shell surrounding the lipid nanoparticle core; and
a linkage connecting the protective shell to the lipid nanoparticle core, wherein the linkage is cleavable by an intracellular stimulus,
the linkage connecting the protective shell to the lipid nanoparticle core comprises:
a shell portion in the protective shell;
a hydrophobic portion in the lipid nanoparticle core;
an intermediate portion linking the shell portion and the hydrophobic portion;
chitosan;
an oleic acid tail; and
a disulfide bond linking the chitosan and the oleic acid tail.

2. The drug delivery vehicle of claim 1, wherein the protective shell comprises an outer layer, and the outer layer has a neutral charge or a negative charge.

3. The drug delivery vehicle of claim 2, wherein the outer layer of the protective shell is breakable by a pH ranging from 6.5 to 6.9.

4. The drug delivery vehicle of claim 2, wherein the outer layer of the protective shell comprises hyaluronic acid.

5. The drug delivery vehicle of claim 1, wherein the protective shell comprises an inner layer, and the inner layer has a positive charge.

6. The drug delivery vehicle of claim 5, wherein the inner layer of the protective shell comprises chitosan.

7. The drug delivery vehicle of claim 1, wherein a space between the lipid nanoparticle core and the protective shell is configured to enclose a secondary drug.

8. The drug delivery vehicle of claim 1, wherein an average size of the drug delivery vehicle ranges from 50 nanometers (nm) to 300 nm.

9. A drug delivery system, comprising:
a drug delivery vehicle comprising
a lipid nanoparticle core, wherein the lipid nanoparticle core encloses a primary drug;
a protective shell surrounding the lipid nanoparticle core; and
a linkage connecting the protective shell to the lipid nanoparticle core, wherein the linkage is cleavable by an intracellular stimulus,
the linkage connecting the protective shell to the lipid nanoparticle core comprises:
a shell portion in the protective shell;
a hydrophobic portion in the lipid nanoparticle core;
an intermediate portion linking the shell portion and the hydrophobic portion;
chitosan;
an oleic acid tail; and
a disulfide bond linking the chitosan and the oleic acid tail.

10. The drug delivery system of claim 9, further comprising:
a secondary drug enclosed between the lipid nanoparticle core and the protective shell.

11. A method of preparing the drug delivery system of claim 9, comprising:
forming the primary drug-enclosing lipid nanoparticle core, comprising mixing:
a component for forming the lipid nanoparticle core; and
the primary drug;
incorporating a component for forming the linkage into the primary drug-enclosing lipid nanoparticle core; and
forming the drug delivery system, wherein forming the drug delivery system comprises mixing the primary drug-containing lipid nanoparticle core; and a component for forming the protective shell.

12. The method according to claim 11, wherein forming the drug delivery system comprises mixing the primary drug-containing lipid nanoparticle core; the component for forming the protective shell; and
a secondary drug, and
wherein, in the drug delivery system, the secondary drug is enclosed in a space formed by the primary drug-containing lipid nanoparticle core and the protective shell.

13. A method of treating cancer, comprising administering to a subject in need thereof the drug delivery system of claim 9, wherein the primary drug comprises a compound that causes or promotes a cancer cell to undergo apoptosis.

14. The method according to claim 13, wherein the drug delivery system further comprises a secondary drug enclosed in a space between the lipid nanoparticle core and the protective shell, and the secondary drug is a compound capable of breaking down an extracellular matrix (ECM).

15. The method according to claim 13, wherein the protective shell comprises an outer layer breakable by a pH ranging from 6.5 to 6.8.

16. The method according to claim 15, wherein the protective shell further comprises an inner layer having a positive charge in a pH ranging from 6.5 to 6.8.

* * * * *